(12) United States Patent
Brandt et al.

(10) Patent No.: US 11,479,578 B2
(45) Date of Patent: Oct. 25, 2022

(54) PROTEIN PURIFICATION AND VIRUS INACTIVATION WITH ALKYL GLYCOSIDES

(71) Applicant: CSL BEHRING LENGNAU AG, Lengnau (CH)

(72) Inventors: Tobias Brandt, Marburg (DE); Hubert Metzner, Marburg (DE); Carsten Horn, Marburg (DE); Thomas Nowak, Staufenberg (DE)

(73) Assignee: CSL Behring Lengnau AG, Lengnau (CH)

( * ) Notice: Subject to any disclaimer, the term of this patent is extended or adjusted under 35 U.S.C. 154(b) by 322 days.

(21) Appl. No.: 16/955,172

(22) PCT Filed: Dec. 19, 2018

(86) PCT No.: PCT/EP2018/085735
§ 371 (c)(1),
(2) Date: Jun. 18, 2020

(87) PCT Pub. No.: WO2019/121846
PCT Pub. Date: Jun. 27, 2019

(65) Prior Publication Data
US 2020/0317727 A1  Oct. 8, 2020

(30) Foreign Application Priority Data
Dec. 19, 2017 (EP) .................................... 17208630

(51) Int. Cl.
*C07K 1/22* (2006.01)
*A61L 2/18* (2006.01)

(52) U.S. Cl.
CPC . *C07K 1/22* (2013.01); *A61L 2/18* (2013.01)

(58) Field of Classification Search
CPC ....................................................... C07K 1/22
See application file for complete search history.

(56) References Cited

U.S. PATENT DOCUMENTS

| 5,432,069 A | 7/1995 | Grüninger et al. |
| 5,759,855 A | 6/1998 | Pierschbacher et al. |

(Continued)

FOREIGN PATENT DOCUMENTS

| AU | 2015204304 | 8/2015 |
| CA | 2228031 | 2/1997 |

(Continued)

OTHER PUBLICATIONS

Brass et al., "Structural Determinants for Membrane Association and Dynamic Organization of the Hepatitis C Virus NS3-4A Complex", Proc Natl Acad Sci USA, 2008, 105(38):14545-14550.

(Continued)

*Primary Examiner* — Jason Y Ko
(74) *Attorney, Agent, or Firm* — Finnegan, Henderson, Farabow, Garrett & Dunner, LLP

(57) ABSTRACT

A process for purifying a recombinant protein comprising the steps of: i) providing a solution comprising the recombinant protein; ii) adding an alkyl glycoside to the solution; and iii) purifying the recombinant protein. The addition of the alkyl glycoside provides improved clearance of process-related impurities. The purified recombinant protein of the invention has low levels of host cell DNA, host cell protein and viral contamination.

33 Claims, 13 Drawing Sheets

(56) References Cited

U.S. PATENT DOCUMENTS

2003/0049819 A1 3/2003 Tjerneld et al.
2010/0216161 A1 8/2010 Taylor

FOREIGN PATENT DOCUMENTS

| WO | WO 97/27873 | 8/1997 |
| --- | --- | --- |
| WO | WO 98/02557 | 1/1998 |
| WO | WO 2004/045641 | 6/2004 |
| WO | WO 2013/010797 | 1/2013 |
| WO | WO 2015/073633 | 5/2015 |
| WO | WO 2016/188907 | 12/2016 |
| WO | WO 2019/028186 | 2/2019 |

OTHER PUBLICATIONS

Heinz et al., "Purification of a cytochrome $aa_3$ terminal oxidase from protoplast membrane vesicles of *Micrococcus luteus*," FEMS—Microbiol—Letters, 1994, 124(2), 173-178.

Almeida et al., "Nasal delivery of vaccines," Journal of Drug Targeting, 1996, 3, 455-467.

Roberts, "Resistance of vaccinia virus to inactivation by solvent/detergent treatment of blood products," Biologicals, 2000, 28, 29-32.

Korneyeva et al., "Enveloped virus inactivation by caprylate: a robust alternative to solvent-detergent treatment in plasma derived intermediates," Biologicals, 2002, 30, 153-162.

Johnston et al., "Low pH, caprylate incubation as a second viral inactivation step in the manufacture of albumin Parametric and validation studies," Biologicals, 2003, 31, 213-221.

Lebing et al., "Low pH, caprylate incubation as a second viral inactivation step in the manufacture of albumin Parametric and validation studies," VoxSang, 2003, 84(3), 193-201.

World Health Organization, "Guidelines on viral inactivation and removal procedures intended to assure the viral safety of human blood plasma products," WHO Technical Report, Annex 4, 2004, Series No. 924, 150-224.

Bosley et al., "A method of HIV-1 inactivation compatible with antibody-based depletion of abundant proteins from plasma," Proteomics Clin Appl, 2008, 2, 904-907.

Garg et al., Glycoside analogs of β-galactosylceramide, a novel class of small molecule antiviral agents that inhibit HIV-1 entry, Antiviral Res, 2008, 80, 1, 54-61.

Bachan et al., "Synthesis, gp120 binding and anti-HIV activity of fatty acid esters of 1,1-linked disaccharides," Bioorganic & Medicinal Chem, 2011, 19, 16, 4803-4811.

Groener et al., "Pathogen safety of human C1 esterase inhibitor concentrate," Transfusion, 2012, 52, 2104-2112.

The extended European search report issued in Application No. 17208630.8, dated Jun. 20, 2018, 8 pages.

International Search Report issued in PCT/EP2018/085735 and the Written Opinion of the International Searching Authority, dated Jun. 5, 2019, 19 pages.

Figure 8

- detection limit
- PRV, 11.9 mg/ml D'D3-FP at 60 mM OG
- held control 17101221
- PRV, 11.9 mg/ml D'D3-FP at 60 mM n-Decyl-ß-D-glucopyranoside
- held control 17101222
- PRV, 11.9 mg/ml D'D3-FP at 60 mM n-Octyl-ß-D-maltoside
- held control 17101223
- PRV, 11.9 mg/ml D'D3-FP at 60 mM n-Dodecyl-ß-D-maltoside
- held control 17101721
- PRV, 11.9 mg/ml D'D3-FP at 60 mM n-Dodecyl-ß-D-glucopyranoside
- held control 17101722
- PRV, 11.9 mg/ml D'D3-FP at 60 mM n-Decyl-ß-D-maltopyranoside
- held control 17101723 a)

PROTEIN PURIFICATION AND VIRUS INACTIVATION WITH ALKYL GLYCOSIDES

This application is the United States national stage entry under 35 U.S.C. § 371 of International Application No. PCT/EP2018/085735, filed on Dec. 19, 2018, which claims priority to European Patent Application No. 17208630.8, filed on Dec. 19, 2017. The contents of these applications are each incorporated herein by reference in their entirety.

TECHNICAL FIELD

This invention is in the field of recombinantly expressed polypeptides, particularly the purification of these polypeptides for pharmaceutical use.

BACKGROUND ART

The large-scale, economic purification of recombinantly expressed polypeptides is increasingly an important problem for the biotechnology industry. These polypeptides are produced by cell culture, generally using either mammalian, yeast or bacterial cell lines engineered to produce the polypeptide of interest by insertion of a recombinant plasmid containing the gene for that polypeptide. Separation of the desired polypeptide from cellular components, e.g. host cell DNA and proteins, to a purity sufficient for use as a human therapeutic poses a formidable challenge. The purification techniques used will ideally be scalable, efficient, cost-effective, reliable, and meet any purity requirements of the final product. Current purification techniques usually involve multiple chromatographic separations. A typical process might include all or at least some of the following steps: precipitation, ultrafiltration, diafiltration, immunoaffinity and affinity chromatography, cation exchange chromatography, anion exchange chromatography, hydrophobic interaction chromatography, multimodal chromatography, metal chelate chromatography, and size exclusion chromatography.

A polypeptide manufactured using recombinant techniques, particularly with mammalian cell lines, may also be contaminated with viruses, including pathogenic viruses that are deleterious to health. It is important to eliminate any contaminating viral activity if the polypeptide is to be administered to an individual. There are currently many different methods for inactivating pathogenic viruses, including, e.g. wet or dry heat-inactivation, solvent/detergent (S/D) inactivation, pH inactivation, chemical inactivation, and/or ultraviolet/gamma irradiation inactivation. Of these, S/D inactivation is perhaps the most widely used virucidal method because nearly all of the significant human pathogens are enveloped viruses susceptible to membrane disruption by solvents and detergents. In the S/D inactivation method, an organic solvent and a detergent are mixed with a fluid including the polypeptide being purified and incubated. The solvent creates an environment promoting aggregation between the detergent and the lipid membrane encapsulating the virus, and the detergent disrupts the interactions between molecules in this lipid membrane. Once disrupted, an enveloped virus can no longer bind to and infect a cell and is unable to reproduce because an intact lipid membrane is essential for such activities. Typical conditions used in accordance with the World Health Organization (WHO) guidelines are 0.3% tri(n-butyl) phosphate (TNBP) and 1% Polysorbate 80 (PS 80, also known as polyoxyethylene (80) sorbitan monooleate or TWEEN® 80) incubated at 24° C. for a minimum of 6 hours, or 0.3% TNBP and 1% polyoxyethylene octyl phenyl ether (TRITON® X-100) incubated at 24° C. for a minimum of 4 hours (see ref. 1).

Although S/D treatment has become the standard technique for inactivating enveloped viruses, its use has some drawbacks. S/D mixtures added during manufacturing must be essentially removed before generation of the final product. For example, TNBP poses a health risk at the concentrations used and, therefore, is a health and safety issue for manufacturing processes and the finished products. Furthermore, conventionally used detergents such as TRITON® X-100 pose a serious environmental threat and have to be discontinued. The incorporation of this virus inactivation step also increases processing times and can decrease product yields by as much as 10% (see ref. 2), and it requires apparatus to agitate the mixture during incubation. To minimize or eliminate these problems, simpler, more efficient virus inactivation procedures have been proposed. A common option involves the use of the fatty acid caprylic acid (octanoate), as proposed for example in refs. 2, 3 and 4. Further options are described in refs. 5 and 6. In particular, ref. 6 tests various detergents that are suggested to be more environmentally compatible. The effects of using different detergents on viral inactivation are variable. Moreover, although a particular detergent might be capable of viral inactivation, its influence on the further purification process cannot be predicted, e.g. in terms of DNA or host cell protein reduction.

There is thus a need for further and improved processes for purifying recombinantly expressed polypeptides, and particularly for processes that achieve reduced DNA and protein contamination, and inactivate pathogenic viruses.

DISCLOSURE OF THE INVENTION

The invention is based on a purification process in which an alkyl glycoside is added to the recombinant polypeptide. The inventors have found that alkyl glycosides, and in particular n-octyl-beta-D-glucopyranoside, may provide improved clearance of process-related impurities during purification steps, e.g. when added to the feed material prior to the purification step. For example, the inventors have discovered that the presence of an alkyl glycoside in the feedstream of a chromatography purification step may result in significantly lower host cell DNA and host cell protein levels at the eluate stage in comparison to the use of alternative agents such as TNBP/PS 80 or control buffer solutions. Moreover, the alkyl glycoside is capable of efficient virus inactivation, even when present for only a short period without any agitation, thereby reducing process time and costs. The process can be carried out under a wide range of process parameters while retaining this efficient virus inactivation. In addition to n-octyl-beta-D-glucopyranoside, the inventors have found that n-decyl-beta-D-glucopyranoside, n-octyl-beta-D-maltoside, n-dodecyl-beta-D-maltoside, n-dodecyl-beta-D-glucopyranoside and n-decyl-beta-D-maltoside are particularly effective alkyl glycosides for use in the invention.

Accordingly, the invention provides a process for purifying a recombinant polypeptide comprising the steps of: i) providing a solution comprising the recombinant polypeptide; ii) adding an alkyl glycoside to the solution; and iii) purifying the recombinant polypeptide.

The recombinant polypeptide will typically be comprised within a solution that further comprises measurable amounts of host cell DNA and/or host cell protein. In these embodiments, the invention provides a process for separating the recombinant polypeptide from the host cell DNA and/or host cell protein, wherein step (iii) results in this separation. The addition of the alkyl glycoside to the solution may improve this separation compared to the same process without the alkyl glycoside, e.g. improving the separation by at least 10% (particularly at least 20%). The inventors have found that particularly effective separation is achievable when step (iii) is performed by carrying out a step of chromatography on the solution. The chromatography may be selected from any suitable chromatography, e.g. immunoaffinity, affinity, hydrophobic interaction, ion exchange, multimodal, size exclusion or metal chelate chromatography. In the modes for carrying out the invention below, the inventors use in particular a step of immunoaffinity chromatography. Hydrophobic interaction chromatography and/or ion exchange chromatography are also particularly useful.

The alkyl glycoside added to the solution comprising the recombinant polypeptide may have a concentration in such solution of preferably between 0.1 and 1000 mM (e.g. between 1 and 500 mM, 3 and 400 mM, 5 and 200 mM, 10 and 100 mM, 20 and 90 mM), and is usually about 25 to 80 mM.

When step (iii) is performed by carrying out a step of chromatography on the solution, the alkyl glycoside may additionally be included in the wash buffer of the chromatography step. In other embodiments, including the alkyl glycoside in the wash buffer of the chromatography step may be used as an alternative to carrying out step (ii) as a separate step. In these embodiments, the invention therefore provides a process for purifying a recombinant polypeptide comprising the steps of: i) providing a solution comprising the recombinant polypeptide; and iii) purifying the recombinant polypeptide by carrying out a step of chromatography on the solution, wherein an alkyl glycoside is included in the wash buffer of the chromatography step. By including the alkyl glycoside in the wash buffer of the chromatography the host cell DNA levels and/or host cell protein (HCP) levels and/or other protein impurities could be further reduced in comparison to a reference process using a corresponding wash buffer without alkyl glycoside.

Further purification steps may be included in the process, either before the step of adding the alkyl glycoside to the solution, or after step (iii). The purification step is typically a step of chromatography. The chromatography may be selected from any suitable chromatography, e.g. immunoaffinity, affinity, hydrophobic interaction, ion exchange, multimodal, size exclusion or metal chelate chromatography.

For example, one or more hydrophobic interaction chromatography steps may be included in the process. Typically, a hydrophobic interaction chromatography step is carried out on the solution after step (iii), particularly when step (iii) is an immunoaffinity chromatography step. Similarly, one or more ion exchange chromatography steps may be included in the process.

Typically, an ion exchange chromatography step is carried out on the solution before the step of adding the alkyl glycoside to the solution. An ion exchange chromatography step may also be carried out on the solution after step (iii), particularly when step (iii) is an immunoaffinity chromatography step. In this embodiment, the immunoaffinity chromatography step is typically followed by a hydrophobic interaction chromatography step (as described above), which is then followed by the ion exchange chromatography step.

For example, the inventors have found that a particularly effective process for separating the recombinant polypeptide from host cell DNA and/or host cell protein comprises the steps of: a) providing a solution comprising the recombinant polypeptide; b) purifying the recombinant polypeptide by carrying out a step of ion exchange chromatography on the solution; c) adding an alkyl glycoside to the solution; d) purifying the recombinant polypeptide by carrying out a step of immunoaffinity chromatography on the solution; e) purifying the recombinant polypeptide by carrying out a step of hydrophobic interaction or multimodal chromatography on the solution; and f) purifying the recombinant polypeptide by carrying out a further step of ion exchange chromatography on the solution.

Accordingly, the invention provides, in a process for purifying a recombinant polypeptide in a solution, the improvement consisting of the addition of an alkyl glycoside to the solution. The addition may result in reduced host cell DNA and/or protein contamination after the process. Additionally or alternatively, the addition may provide efficient virus inactivation. Further, the yield of the recombinant polypeptide obtained by the process may be improved.

The invention also provides the use of an alkyl glycoside as an additive to a solution comprising a recombinant polypeptide. The use may result in reduced host cell DNA and/or protein contamination after subsequently purifying the recombinant polypeptide. Additionally or alternatively, the use may provide and efficient virus inactivation.

The process of the invention may provide a solution of the recombinant polypeptide comprising a level of host cell DNA contamination that is less than 5000 pg/ml (e.g. ≤4000 pg/ml, ≤3000 pg/ml, ≤2500 pg/ml, ≤2000 pg/ml, ≤1500 pg/ml, ≤1000 pg/ml, ≤500 pg/ml, ≤200 pg/ml, ≤100 pg/ml, ≤50 pg/ml etc.). Typically, the level of host cell DNA contamination is less than 500 pg/ml, particularly less than 200 pg/ml.

The process of the invention may provide a solution of the recombinant polypeptide comprising a level of host cell DNA contamination that is reduced by a factor of at least 1.5, preferably at least 2, at least 5, at least 10, at least 20, at least 50, at least 100, at least 150 or at least 200, when compared to a reference process which is identical to the process of the invention with the exception that no alkyl glycoside is used or with the exception that a conventional S/D treatment such as TNBP/PS 80 is used.

The process of the invention may provide a solution of the recombinant polypeptide, preferably following the purification of the recombinant polypeptide according to step iii), comprising a level of host cell DNA contamination that is reduced by a factor of at least 10, preferably at least 100, at least 1000, at least 10,000, at least 15,000, at least 20,000 or at least 25,000, when compared to the level of host cell DNA contamination before purification of the recombinant polypeptide, preferably according to step iii). Such reductions are seen when step (iii) is an immunoaffinity chromatography step, for example.

The process of the invention may provide a solution of the recombinant polypeptide comprising a level of host cell protein (HCP) contamination that is less than 5000 ng/ml (e.g. ≤4000 ng/ml, ≤3500 ng/ml, ≤3000 ng/ml, ≤2500 ng/ml, ≤2000 ng/ml, ≤1800 ng/ml, ≤500 ng/ml, ≤1000 ng/ml etc.). Typically, the level of host cell protein contamination is less than 5000 ng/ml, particularly less than 3000 ng/ml.

The process of the invention may provide a solution of the recombinant polypeptide comprising a level of host cell protein (HCP) contamination that is reduced by a factor of at least 1.5, preferably at least 2, at least 2.5, at least 3, or at least 3.5, when compared to a reference process which is identical to the process of the invention with the exception that no alkyl glycoside is used or with the exception that a conventional S/D treatment such as TNBP/PS 80 is used.

The process of the invention may provide a solution of the recombinant polypeptide, preferably following the purification of the recombinant polypeptide according to step iii), comprising a level of host cell protein (HCP) contamination that is reduced by a factor of at least 10, preferably at least 100, at least 200, at least 300, at least 400, at least 500, at least 700, at least 800, at least 900, or at least 1,000, when compared to the level of host cell protein contamination before purification of the recombinant polypeptide, preferably according to step iii). Such reductions are seen when step (iii) is an immunoaffinity chromatography step, for example.

In particular, the process of the invention may provide a solution of the recombinant polypeptide wherein: (a) the level of host cell DNA contamination is less than 5000 pg/ml (as described above); and (b) the level of host cell protein (HCP) contamination is less than 5000 ng/ml (as described above).

The process of the invention may provide a solution of the recombinant polypeptide, wherein the yield of the obtained recombinant polypeptide is improved by a factor of at least 1.05, 1.1, 1.2, 1.3, 1.4, 1.5, 1.6, 1.7, 1.8, 1.9 or at least 2, when compared to the yield of the recombinant polypeptide obtained by a reference process which is identical to the process of the invention with the exception that no alkyl glycoside is used or with the exception that a conventional S/D treatment such as TNBP/PS 80 is used.

The solution of the recombinant polypeptide according to one or more of the herein mentioned processes is preferably provided as a result of a purification of the recombinant polypeptide as described herein, particularly as a result of the purification according to step iii). Alternatively or in addition, the alkyl glycoside may be included in the wash buffer of a chromatography step.

The invention also provides a solution comprising a recombinant polypeptide and an alkyl glycoside, in particular a solution obtained or obtainable from step (ii) of the process of the invention.

The invention also provides a solution comprising a purified recombinant polypeptide, in particular a solution obtained or obtainable from the process of the invention. The solution may contain a residual amount of alkyl glycoside. The amount of alkyl glycoside may be below the limit of detection, e.g. when using mass spectroscopy. For example, the amount of alkyl glycoside may be less than 1.5 µg/ml (or less than 40 ng/mg of purified recombinant polypeptide). The amount of alkyl glycoside may in particular be less than 10 ng/mg of purified recombinant polypeptide.

The invention also provides a solution comprising a recombinant polypeptide, wherein the solution comprises a level of host cell DNA contamination that is less than 5000 pg/ml (e.g. ≤4000 pg/ml, ≤3000 pg/ml, ≤2500 pg/ml, ≤2000 pg/ml, ≤1500 pg/ml, ≤1000 pg/ml, ≤500 pg/ml, ≤200 pg/ml, ≤100 pg/ml, ≤50 pg/ml etc.). Typically, the level of host cell DNA contamination is less than 500 pg/ml, particularly less than 200 pg/ml.

The invention also provides a solution comprising a recombinant polypeptide, wherein the solution comprises a level of host cell protein contamination that is less than 5000 ng/ml (e.g. ≤4000 ng/ml, ≤3500 ng/ml, ≤3000 ng/ml, ≤2500 ng/ml, ≤2000 ng/ml, ≤1800 ng/ml, ≤1500 ng/ml, ≤1000 ng/ml etc.). Typically, the level of host cell protein contamination is less than 5000 ng/ml, particularly less than 3000 ng/ml.

The invention also provides a solution comprising a recombinant polypeptide, wherein: (a) the level of host cell DNA contamination is less than 5000 pg/ml (as described above); and (b) the level of host cell protein contamination is less than 5000 ng/ml (as described above).

The invention also provides the use of an alkyl glycoside as an additive to a solution comprising a recombinant polypeptide wherein the alkyl glycoside is added without any organic solvent such as TNBP. Organic solvents in this context may for example be any carbon-based solvents. According to the invention, the alkyl glycoside may be provided without prior mixing with a solvent other than water or other than aqueous buffer solutions or the like.

The invention also provides the use of an alkyl glycoside as an additive to a wash buffer for a chromatography step as described herein.

The invention also provides a wash buffer for use in a chromatography step, whereby the buffer comprises an alkyl glycoside as an additive. The wash buffer is preferably configured to be applicable in a process for purifying a recombinant polypeptide according to the invention.

The alkyl glycoside may have a concentration in such wash buffer of between 0.1 and 1000 mM (e.g. between 0.2 and 500 mM, 0.5 and 300 mM, 1 and 200 mM, 1.5 and 100 mM, 2 and 80 mM), and is usually about 10 to 100 mM.

Thus, according to a preferred embodiment of the invention, a solution comprising the recombinant polypeptide is provided and may be incubated if required; the solution is used to load a chromatography column and prior to elution the column is washed with a wash buffer containing an alkyl glycoside. The final concentration of alkyl glycoside in the wash buffer is typically between 0.1 and 1000 mM (e.g. between 0.2 and 500 mM, 0.5 and 300 mM, 1 and 200 mM, 1.5 and 100 mM, 2 and 80 mM), and is usually about 10 to 100 mM. The inventors have found that in this case the concentration may also be below the critical micelle concentration (CMC) of the alkyl glycoside. Using this wash procedure the host cell DNA and/or the HCP and/or other protein impurities could be reduced by more than 5-fold, more than 10-fold, more than 25-fold, more than 50-fold or even more than 100-fold in comparison to a reference process using a corresponding wash buffer without alkyl glycoside. A more than 100-fold reduction of such a protein impurity is demonstrated in below example 3. A protein impurity may be for example one or more fragments of the recombinant polypeptide of interest, a propeptide of the recombinant polypeptide of interest, any co-expressed protein etc.

In another aspect of the invention, the inventors have found that alkyl glycosides have particularly advantageous effects when used for viral inactivation. Enveloped viruses are sensitive to the alkyl glycosides, and compared to alternative agents such as TNBP/PS 80, alkyl glycosides suffer from little or no loss of inactivation ability when used at low temperatures. They can even be used without agitation, e.g. without shaking. Exemplary alkyl glycosides for this purpose are n-octyl-beta-D-glucopyranoside, n-decyl-beta-D-glucopyranoside, n-octyl-beta-D-maltoside, n-dodecyl-beta-D-maltoside, n-dodecyl-beta-D-glucopyranoside and n-decyl-beta-D-maltoside, with n-octyl-beta-D-glucopyranoside being particularly effective.

This further aspect of the invention may be applied with the process of the invention for purifying a recombinant polypeptide. For example, step ii) of that process (i.e. adding an alkyl glycoside to the solution comprising the recombinant polypeptide) may further comprise incubating the solution. The incubation results in inactivation of one or more viruses that may be in the solution. The incubation can be carried out as described below. The viruses will typically be contaminating viruses that enter the solution from the environment or were present in material from which the solution was made. The presence or absence of the viruses in the solution may not be known, and so the invention can be used to reduce the risk of viral contamination by inactivating one or more viruses that may be in the solution. When viruses are present in the solution, the incubation results in inactivation of one or more of these viruses.

Alternatively, this aspect of the invention may be applied as a standalone process. In this way, the invention provides a process for inactivating one or more viruses that may be in a solution comprising a recombinant polypeptide comprising a step of adding an alkyl glycoside to the solution and incubating the solution. The one or more viruses are typically enveloped viruses. The incubation may be carried out for any suitable length of time, typically for as long as it takes to achieve effective viral reduction. The achieved virus reduction factor in logo may for example be at least 4. In typical embodiments, the incubation is carried out for between 1 minute and 24 hours, between 2 minutes and 12 hours, preferably between 10 minutes and 5 hours, and usually for about 30 minutes or more. The incubation is conveniently carried out at room temperature, although good results can also be achieved at lower temperatures, e.g. ≤20° C., and even between 4 and 10° C. These lower temperatures are particularly advantageous if the protein is sensitive to temperature. The final concentration of alkyl glycoside before incubation is typically between 0.1 and 1000 mM (e.g. between 1 and 500 mM, 3 and 400 mM, 5 and 200 mM, 10 and 100 mM, 20 and 90 mM), and is usually about 25 to 80 mM. The inventors have found that a concentration above the critical micelle concentration (CMC) of the alkyl glycoside is useful, particularly for viral inactivation. Typically the concentration will be 1.5, 2, 3 or 4 times above this CMC.

This process for inactivating one or more viruses has been described above in relation to a solution comprising a recombinant polypeptide. However, the skilled person will understand that the process can be applied to any suitable feed material, in particular (human) plasma-derived material or the like. Plasma-derived material is particularly prone to viral contamination. Accordingly, in a more general aspect, the invention provides a process for inactivating one or more viruses that may be in a solution comprising a step of adding an alkyl glycoside to the solution and incubating the solution. The solution may in particular be derived from a biological composition such as whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascitic fluid, proteins present in blood cells, and products produced in cell culture by normal or transformed cells (e.g., via recombinant DNA or monoclonal antibody technology).

According to a preferred embodiment the alkyl glycoside is used for inactivating one or more enveloped viruses, in particular in one or more of the herein described processes, whereby the one or more viruses are preferably selected from the group consisting of MuLV (murine leukemia virus), BVDV (bovine viral diarrhea virus), PRV (pseudorabies virus), VSV (Vesicular Stomatitis Virus) and VACV (Vaccinia virus).

The Recombinant Polypeptide

The term "polypeptide" is used herein to refer to polymers of amino acids of any length. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, sulfation or any other manipulation or modification, such as conjugation with a labeling or half-life extending component. Also included within the term are, for example, polypeptides containing one or more analogs of an amino acid (including, for example, unnatural amino acids, etc.), as well as other modifications known in the art. The polypeptide may be in the form of a multimer of individual polypeptides.

The polypeptide of the invention may be any polypeptide of interest, particularly one in which elimination of any contaminating viral activity is desired. The polypeptide of the invention may preferably be a water soluble polypeptide, particularly not a membrane-inserted polypeptide.

The polypeptide may be any polypeptide of therapeutic interest. The polypeptide may be in particular selected from the group comprising an antibody, a blood protein, an enzyme, a receptor, a hormone, a regulatory factor, an antigen, a cytokine, and other polypeptides of interest. E.g., it may be a monoclonal antibody, domains thereof, dimers or oligomers of such antibodies or domains thereof, a bispecific antibody, a single chain antigen binding domain (ScFv), or a chimeric polypeptide.

The polypeptide may in particular also be a blood protein, e.g. a coagulation protein, albumin, or an immunoglobulin. Non-limiting examples of a blood protein include ADAMTS-13, α1-antiplasmin, α2-antiplasmin, antithrombin III, cancer procoagulant, erythropoietin, Factor II, Factor V, Factor VII, Factor VIII, Factor IX, Factor X, Factor XI, Factor XII, Factor XIII, fibronectin, fibrinogen, heparin cofactor II, high-molecular-weight kininogen, immunoglobulin, plasminogen, plasminogen activator inhibitor-1, plasminogen activator inhibitor-2, prekallikrein, protein C, protein S, protein Z, protein Z-related protease inhibitor, tissue factor, tissue plasminogen activator, urokinase, or Von Willebrand Factor. The polypeptide may be a fusion protein thereof.

The polypeptide may also be a variant of naturally-occurring polypeptide, for example a variant of one of the polypeptides described above. A variant may comprise fragments of said naturally-occurring polypeptide. The inventors originally developed the process of the invention for purifying recombinant variants of Von Willebrand Factor fusion proteins. The general class of variants is described in ref. 7, and the "D'D3-FP" variant from this document (where it is designated SEQ ID NO: 2) is the representative polypeptide that the inventors used in the modes for carrying out the invention below.

The polypeptide may be fused to a heterologous amino acid sequence. Said heterologous amino acid sequence comprises or consists of a polypeptide selected from the group consisting of immunoglobulin constant regions and portions thereof, e.g. the Fc fragment, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, and combinations thereof. According to a preferred embodiment the polypeptide is fused to albumin or an Fc fragment, in particular to albumin.

The polypeptide may alternatively or in addition be conjugated to a further moiety. Said moiety is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains or albumin binding peptides, and combinations thereof.

The term "recombinant polypeptide" is used herein to refer to a polypeptide that has been recombinantly expressed. In particular, the polypeptide has been obtained from a transgenic organism genetically-engineered to express the polypeptide, or from a cell line recombinantly producing the polypeptide. Non-limiting examples of an organism include birds and mammals, such as, e.g. mice, rats, goats, sheep, horses, donkeys, cows, primates and humans. Non-limiting examples of a transgenic organism include organisms that have been genetically-engineered to express the polypeptide. A polypeptide from a transgenic organism may be obtained from a biological fluid, tissue or organ extract, or other source from an organism using routine methods known in the art. More typically, however, a prokaryote and/or eukaryotic expression system is used to recombinantly express the polypeptide. Expression systems can include any of a variety of characteristics including, without limitation, inducible expression, non-inducible expression, constitutive expression, tissue-specific expression, cell-specific expression, viral-mediated expression, stably-integrated expression, and transient expression. How to make and use such expression systems are known in the art.

Generally, a polynucleotide encoding the polypeptide of interest is cloned into an expression vector. Prokaryote expression vectors typically comprise an origin of replication, a suitable promoter and/or enhancer elements, and also sites necessary for ribosome binding, polyadenylation, transcriptional termination, as well as 5' flanking non-transcribed sequences and other non-transcribed genetic elements. Exemplary prokaryotic vectors include pET and pRSET using promoters such as, e.g. a bacteriophage T7 promoter. Eukaryotic expression vectors typically comprise an origin of replication, a suitable promoter and/or enhancer elements, and also sites necessary for ribosome binding, polyadenylation, splicing, transcriptional termination, as well as 5' flanking non-transcribed sequences and other non-transcribed genetic elements. Exemplary yeast vectors include pAO, pMET, pPIC, pPICZ, and pYES using promoters such as, e.g. AOX1, AUG1, GAP, and GALL. Exemplary insect vectors include pAc5, pBAC, pIB, pMIB, pMT, using promoters such as, e.g. PH, p10, MT, Ac5, OpIE2, gp64, and polh. Exemplary mammalian vectors include pBPV, pCMV, pCMVTNT, pDNA, pDisplay, pMSG, pOG44, PQBI25, pRc/RSV, pSECTag, pSECTag2, pSG, pSV2cat, pSVK3, pSVL, pUCIG-MET, pVAX1, pWLneo, and pXT1 using promoters such as, e.g. beta-casein, beta-lactoglobulin, whey acid promoter, HSV thymidine kinase, early and late simian virus 40 (SV40), LTRs from retrovirus, and mouse metallothionein-1. Selectable markers include Ampicillin, Chloramphenicol transferase, Kanamycin, Neomycin, and Tetracycline. Suitable expression vectors are known in the art and commercially available.

Cells capable of expressing a compatible vector include prokaryotic cells, eukaryotic cells, and cell lines derived from prokaryotic and eukaryotic cells. Non-limiting examples of prokaryotic strains include those derived from, e.g. *Escherichia coli, Bacillus subtilis, Bacillus licheniformis, Bacteroides fragilis, Clostridia perfringens, Clostridia difficle, Caulobacter crescentus, Lactococcus lactis, Methylobacterium extorquens, Neisseria meningirulls, Neisseria meningitidis, Pseudomonas fluorescens* and *Salmonella typhimurium*. Non-limiting examples of yeast strains include those derived from, e.g. *Pichia pastoris, Pichia methanolica, Pichia angusta, Schizosaccharomyces pombe, Saccharomyces cerevisiae* and *Yarrowia lipolytica*. Plant cells and cell lines derived from plants include cells from, e.g. species of monocots, such as, e.g. *Zea mays* and species of dicots, such as, e.g. *Arabidopsis thaliana, Triticum aestivum, Lemna gibba* and *Lemna minor*. Insect cells and cell lines derived from insects include cells from, e.g. *Spodoptera frugiperda, Trichoplusia ni, Drosophila melanogaster* and *Manduca sexta*. Non-limiting examples of insect cell lines include High-Five, Kc, Schneider's *Drosophila* line 2 (S2), SF9, and SF21 cell lines. Mammalian cells and cell lines derived from mammalian cells include cells from, e.g. mouse, rat, hamster, porcine, bovine, equine, primate and human. Non-limiting examples of mammalian cell lines include 1A3, 3T3, 6E6, 10T1/2, APRT, BALB/3T3, BE(2)-C, BHK, BT, C6, C127, CHO, CHP3, COS-1, COS-7, CPAE, ESK-4, FB2, GH1, GH3, HeLa, HEK-293, HepG2, HL-60, IMR-32, L2, LLC-PK1, L-M, MCF-7, NB4, NBL-6, NCTC, Neuro 2A, NIE-1 15, NG108-15, NIH3T3, PC12, PK15, SBAC, SH-SY5Y, SK-Hep, SK-N-DZ, SK-N-F1, SK-N-SH, ST, SW-13, and VV-1 cell lines. Cell lines may be obtained from the American Type Culture Collection, European Collection of Cell Cultures and/or the German Collection of Microorganisms and Cell Cultures.

The recombinant polypeptide will typically be comprised within a solution comprising host cell DNA and/or host cell protein (most typically both). The solution is typically an aqueous solution, because polypeptides occur in an aqueous environment in nature. The host cell DNA and/or host cell protein is present in the solution from the transgenic organism or cell line that recombinantly expressed the polypeptide. When the polypeptide was expressed by a cell line, the solution may comprise culture medium from the cell line culture. The recombinant polypeptide may have been transferred to a particular medium for subsequent purification.

Typically, the amount of host cell DNA in the solution comprising the recombinant polypeptide in step (i) is between 0.01 µg/ml and 100 µg/ml, e.g. between 0.1 µg/ml and 50 µg/ml. Similarly, the amount of host cell protein in step (i) is typically between 5 µg/ml and 5 mg/ml, e.g. between 50 µg/ml and 1000 µg/ml. As discussed above, it is usual for both of these contaminating species to be present, such that the solution has between 0.01 and 100 µg/ml of host cell DNA (as described above, e.g. at least 100 µg/ml) and between 5 µg/ml and 5 mg/ml of host cell protein (as described above, e.g. at least 100 ng/ml).

Purification Steps Prior to Addition of the Alkyl Glycoside

As discussed above, further purification steps may be included in the process, either before the step of adding the alkyl glycoside to the solution, or after step (iii). Each further purification step is typically a step of chromatography. The chromatography may be selected from any suitable chromatography, e.g. immunoaffinity, affinity, hydrophobic interaction, ion exchange, multimodal, size exclusion or metal chelate chromatography.

For example, an ion exchange chromatography step may be carried out on the solution before the step of adding the alkyl glycoside to the solution. An example of this approach is provided in the modes for carrying out the invention below. The inventors have found that anion exchange chromatography (as described below) is particularly suitable for this step, e.g. with a Poros™ XQ chromatography matrix.

The invention typically uses anion exchange chromatography as the ion exchange chromatography. In anion exchange chromatography, negatively charged molecules are attracted to a positively charged solid support. A positively charged solid support can be prepared by any means known to persons skilled in the art and will usually involve the covalent attachment of a positively charged functional ligand onto a solid support. Suitable positively charged functional ligands will invariably depend on the polypeptide to be separated from solution. Examples of suitable anion exchange resins are ones comprising a functional quaternary amine group (Q) and/or a tertiary amine group (DEAE), or a diethylaminopropyl group (ANX). Commercially available anion exchange chromatography matrices include, but are not limited to, DEAE cellulose, Poros™ PI 20, PI 50, HQ 10, HQ 20, HQ 50, D 50, XQ from ThermoFisher, MonoQ™, MiniQ™, Source™ 15Q and 30Q, Q, DEAE and ANX Sepharose Fast Flow™, Q Sepharose high Performance™, QAE SEPHADEX™ and FAST Q SEPHAROSE™ from GE Healthcare, WP PEI™, WP DEAM™, WP QUAT™ from J. T. Baker, Hydrocell™ DEAE and Hydrocell™ QA from Biochrom Labs Inc., UNOsphere™ Q, Macro-Prep™ DEAE and Macro-Prep™ High Q from Biorad, Ceramic HyperD™ Q, ceramic HyperD™ DEAE, Q HyperZ™, Trisacryl™ M and LS™ DEAE, Spherodex™ LS DEAE, QMA Spherosil™ LS, QMA Spherosil™ M from Pall Technologies, DOWEX™ Fine Mesh Strong Base Type I and Type II Anion Matrix and DOWEX™ MONOSPHER E 77, weak base anion from Dow Liquid Separations, Matrex Cellufine™ A200, A500, Q500, and Q800, from Millipore, Fractogel™ EMD TMAE$_3$, Fractogel™ EMD DEAE and Fractogel™ EMD DMAE from EMD, Amberlite™ weak and strong anion exchangers type I and II, DOWEX™ weak and strong anion exchangers type I and II, Diaion™ weak and strong anion exchangers type I and II, Duolite™ from Sigma-Aldrich, TSK™ gel Q and DEAE 5P and 5PW-HR, Toyopearl™ SuperQ-6505, 650M and 650C$_3$ QAE-26-550C and 650S, DEAE-650M and 650C from Tosoh, and QA52™, DE23™, DE32™, DE51™, DE52™, DE53™, Express-Ion™ D and Express-Ion™ Q from Whatman.

If desirable, an anion exchange chromatography membrane can be used instead of an anion exchange chromatography matrix. Commercially available anion exchange membranes include, but are not limited to, Sartobind™ Q from Sartorius, Mustang™ Q from Pall Technologies and Intercept™ Q membrane from Millipore.

As an alternative to anion exchange chromatography, it may be possible in some embodiments to use cation exchange chromatography. In cation exchange chromatography, positively charged molecules are attracted to a negatively charged solid support. Any negatively charged ligand attached to the solid phase suitable to form the cation exchange matrix can be used, e.g. a carboxylate, sulfonate and others as described below. Commercially available cation exchange matrices include, but are not limited to, for example, those having a sulfonate based group (e.g. MonoS®, MiniS, Source™ 15S and 30S, SP Sepharose® Fast Flow™, SP Sepharose® High Performance from GE Healthcare, Toyopearl® SP-650S and SP-650M from Tosoh, Macro-Prep® High S from BioRad, Ceramic HyperD® S, Trisacryl® M and LS SP and Spherodex® LS SP from Pall Technologies); a sulfoethyl based group (e.g. Fractogel® SE from EMD Millipore, POROS® (S-10 and S-20 from ThermoFisher)); a sulphopropyl based group (e.g. TSK Gel® SP 5PW and SP-5PW-HR from Tosoh, POROS® HS-20 and HS 50 from ThermoFisher); a sulfoisobutyl based group (e.g. Fractogel® EMD S03 from EMD Millipore); a sulfoxyethyl based group (e.g. SE52, SE53 and Express-Ion™ S from Whatman), a carboxymethyl based group (e.g. CM Sepharose® Fast Flow from GE Healthcare, Hydrocell CM from Biochrom Labs Inc., Macro-Prep® CM from BioRad, Ceramic HyperD® CM, Trisacryl M CM, Trisacryl LS CM, from Pall Technologies, Matrex Cellufine C500 and C200 from Millipore, CM52, CM32, CM23 and Express—Ion™ C from Whatman, Toyopearl® CM-650S, CM-650M and CM-650C from Tosoh); sulfonic and carboxylic acid based groups (e.g. BAKERBOND® Carboxy-Sulfon from J. T. Baker); a carboxylic acid based group (e.g. WP CBX from J. T Baker, DOWEX® MAC-3 from Dow Liquid Separations, Amberlite™ Weak Cation Exchangers, DOWEX® Weak Cation Exchanger, and Diaion Weak Cation Exchangers from Sigma-Aldrich and Fractogel® EMD COO- from EMD); a sulfonic acid based group (e.g. Hydrocell SP from Biochrom Labs Inc., DOWEX® Fine Mesh Strong Acid Cation Matrix from Dow Liquid Separations, UNOsphere® S, WP Sulfonic from J. T. Baker, Sartobind® S membrane from Sartorius, Amberlite™ Strong Cation Exchangers, DOWEX® Strong Cation and Diaion Strong Cation Exchanger from Sigma-Aldrich); and a orthophosphate based group (e.g. PI 1 from Whatman).

If desirable, a cation exchange membrane can be used instead of a cation exchange matrix, e.g. Sartobind® S (Sartorius; Edgewood, N.Y.).

Alternatively, an immunoaffinity chromatography step may be carried out on the solution before the step of adding the alkyl glycoside to the solution.

Immunoaffinity chromatography uses the high specificity of an antigen-antibody interaction to isolate and purify polypeptides. The immunoaffinity chromatography step in the present invention typically involves antibodies or antibody fragments immobilized on a solid support over which the solution comprising the recombinant polypeptide is passed and the polypeptide, specific for the immobilized antibody, is captured. Non-specific proteins and peptides are washed away and the antigen is then eluted. In other embodiments, e.g. when the recombinant polypeptide is itself an antibody, the specific antigen for that antibody can be coupled to the column and the solution of the antibody is passed over the column.

The antibody (or in the other embodiments, antigen) can be immobilized to the solid support by numerous techniques, including chemical coupling of the antibody or antigen to an activated solid support through amines or sulfhydryl residues. There are various commercial activated agaroses that are commercially available, using various different coupling chemistries. Another technique uses a solid support coated with an antibody binding protein, such as Protein A or G, which captures and immobilizes the antibody. The antibody is then covalently linked to the resin with the aid of a chemical cross-linker.

In the present invention, an immunoaffinity chromatography step can be used to further reduce host cell protein. This step often maintains a good yield of polypeptide, e.g. around 60-90%. The process typically uses an immunoaffinity chromatography column. The column load can be calculated based on the concentration of recombinant polypeptide in the solution, e.g. by UV absorption. In some embodiments, the solution is conditioned before the immunoaffinity chromatography step, e.g. by addition of disodium edetate (EDTA) or sodium citrate.

Alternatively, an affinity chromatography step may be carried out on the solution before the step of adding the alkyl glycoside to the solution.

Affinity chromatography is a separation method based on a specific binding interaction between an immobilized ligand and its binding partner. Examples include antibody/antigen, enzyme/substrate, and enzyme/inhibitor interactions. The degree of purification can be high depending on the specificity of the interaction and, consequently, affinity chromatography can sometimes be the only step in a purification strategy.

Affinity chromatography can be broadly divided into two approaches. The first approach uses a naturally occurring structure or sequence of amino acids on the polypeptide of interest as the binding site. Examples of affinity chromatography materials include materials derivatized with protein A or protein G. Other options include specifically developed binders (peptides, modified peptides, nucleic acids, synthetic compounds and the like) that allow sufficiently strong binding to the polypeptide and thus can act as binders in an affinity resin. The second method involves binding to a special amino acid sequence engineered into the polypeptide of interest, commonly referred to as a "tag". A number of different tags are available. Two of the most commonly used protein tags are the polyhistidine tag, which binds to certain metal-containing complexes such as those in IMAC resins, and the glutathione s-transferase (GST) sequence, which binds to glutathione, found in GST media.

Particular examples of affinity chromatography materials include Prosep-VA, Prosep-VA Ultra Plus (Merck), Protein A sepharose fast flow, MAbSelect, MAbSelect SuRe, MAbSelect SuRe LX, VIII Select, Capto Blue, Capto Heparin (GE Healthcare), Toyopearl Protein A (Tosoh), CaptureSelect Human Albumin or other CaptureSelect resins (ThermoFisher Scientific), Mimetic Blue SA and Albupure (Prometic). Furthermore, custom affinity resins by companies such as ThermoFisher, Merck or Avitide can be used. The affinity chromatography material may be used in the form of an affinity chromatography column. In other embodiments, the affinity chromatography material is used in the form of an affinity chromatography membrane.

The Alkyl Glycoside

The term "alkyl glycoside" is used herein to refer generally to any sugar joined by a linkage to any hydrophobic alkyl, as is known in the art. The linkage between the hydrophobic alkyl chain and the hydrophilic saccharide can include, among other possibilities, a glycosidic, ester, thioglycosidic, thioester, ether, amide or ureide bond or linkage. Typical options for the sugar in the present invention include glucose (as glucopyranoside) and maltose. Typical options for the hydrophobic alkyl include n-octyl, n-decyl and n-dodecyl groups. The linkage can in particular be a glycosidic linkage, especially a beta glycosidic linkage (e.g. a beta-D glycosidic linkage). The inventors have in particular used an alkyl glycoside wherein the sugar is glucose, the hydrophobic alkyl is a n-octyl group and the linkage is a beta-D glycosidic linkage. Other respective combinations that the inventors have used include: glucose, a n-decyl group and a beta-D glycosidic linkage; maltose, a n-octyl group and a beta-D glycosidic linkage; maltose, a n-dodecyl group and a beta-D glycosidic linkage; glucose, a n-dodecyl group and a beta-D glycosidic linkage; and maltose, a n-decyl group and a beta-D glycosidic linkage.

A general structure for alkyl glycosides that may be used in the invention is $R_1$—O—$(CH_2)_x$—R, where R may be, for example, $CH_3$, cyclohexyl ($C_6H_{11}$), or another alkyl chain, including the isomers thereof, x is typically between 5 and 13, especially between 7 and 11, and $R_1$ is a sugar, typically glucose or maltose. Preferably, the alkyl glycoside used in the invention is n-octyl-β-D-glucopyranoside (i.e. $R_1$ is glucose, R is $CH_3$, and x is 7). The inventors consider this as a preferred option because n-octyl-β-D-glucopyranoside is a mild detergent with favourable physico-chemical and toxicological properties. Other alkyl glycosides that the inventors have used include n-decyl-beta-D-glucopyranoside (i.e. $R_1$ is glucose, R is $CH_3$, and x is 9), n-octyl-beta-D-maltoside (i.e. $R_1$ is maltose, R is $CH_3$, and x is 7), n-dodecyl-beta-D-maltoside (i.e. $R_1$ is maltose, R is $CH_3$, and x is 11), n-dodecyl-beta-D-glucopyranoside (i.e. $R_1$ is glucose, R is $CH_3$, and x is 11) and n-decyl-beta-D-maltoside (i.e. $R_1$ is maltose, R is $CH_3$, and x is 9).

Exemplary alternative alkyl glycosides include those in which $R_1$ is glucose, R is $CH_3$, and x is: 5 (n-hexyl-β-D-glucopyranoside); 6 (n-heptyl-β-D-glucopyranoside); or 8 (n-nonyl-β-D-glucopyranoside). Sometimes glucopyranosides are called glucosides.

Exemplary alkyl glycosides additionally include those in which $R_1$ is maltose, R is $CH_3$, and x is: 5 (n-hexyl-β-D-maltoside); 8 (n-nonyl-β-D-maltoside); 10 (n-undecyl-β-D-maltoside); 12 (n-tridecyl-β-D-maltoside); 13 (n-tetradecyl-β-D-maltoside) or 15 (n-hexadecyl-β-D-maltoside). Sometimes maltosides are called maltopyranosides.

Exemplary alkyl glycosides further include those in which $R_1$ is glucose, x is 3, and R is cyclohexyl (3-cyclohexyl-1-propyl-β-D-glucoside) and in which $R_1$ is maltose, x is 4, and R is cyclohexyl (4-cyclohexyl-1-butyl-β-D-maltoside).

The skilled person in the art will understand that the chemical synthesis of alkyl glycosides such as these may result in a heterogeneous mixture of compounds, rather than a completely homogeneous preparation. As such, references herein to a particular alkyl glycoside being used mean that at least the majority component of any heterogeneous mixture is that alkyl glycoside.

Addition of the Alkyl Glycoside to the Solution Comprising the Recombinant Polypeptide The solution comprising the recombinant polypeptide is treated with an alkyl glycoside as described above. In particular embodiments the alkyl glycoside is n-octyl-β-D-glucopyranoside. This treatment can be conveniently achieved by mixing the solution with a stock solution of the alkyl glycoside, e.g. at 10× the intended final concentration. Unlike solvent/detergent treatment, e.g. with TNBP/PS 80, the alkyl glycoside can be provided in an aqueous solution; it does not require an additional solvent, particularly an organic solvent like TNBP. When the alkyl glycoside is n-octyl-β-D-glucopyranoside, it is convenient to use a stock solution with a concentration between 200 and 1000 mM. If the solution comprising the recombinant polypeptide is the eluate from a chromatography step, then the solution may be diluted with further elution buffer prior to addition of the alkyl glycoside if desired.

The final concentration of alkyl glycoside is typically between 0.1 and 1000 mM (e.g. between 1 and 500 mM, 3 and 400 mM, 5 and 200 mM, 10 and 100 mM, 20 and 90 mM). For n-octyl-β-D-glucopyranoside, the final concentration is usually about 25 to 80 mM. The skilled person would be capable of identifying suitable concentrations for other alkyl glycosides. Optimal concentrations may be identified by testing a range of such concentrations. The inventors have found that a concentration above the critical micelle concentration (CMC) of the alkyl glycoside is useful, particularly for viral inactivation. Typically the concentration will be 1.5, 2, 3 or 4 times above this CMC.

After addition of the alkyl glycoside, the mixture is preferably homogenised to ensure good mixing. This homogenisation typically takes between 2 and 10 minutes.

The mixture is typically filtered (e.g. using a 0.45/0.2 µm filter pore size), which is advantageous because it ensures removal of particles potentially shielding viruses from the alkyl glycoside treatment. The inventors have found that this step maintains a good yield of polypeptide, e.g. around 90-100%.

The mixture may be incubated to allow for viral inactivation, as described above. The incubation may be carried out for any suitable length of time, typically for as long as it takes to achieve effective viral reduction. The achieved virus reduction factor in logo may for example be at least 4. In typical embodiments, the incubation is carried out for between 1 minute and 24 hours, between 2 minutes and 12 hours, preferably between 10 minutes and 5 hours, and usually for about 30 minutes or more. The incubation is conveniently carried out at room temperature, although good results can also be achieved at lower temperatures, e.g. ≤20° C., and even between 4° C. and 10° C. These lower temperatures are particularly advantageous if the protein is sensitive to temperature. Care should be taken not to incubate the mixture at a temperature that might denature the recombinant polypeptide (if activity is to be preserved). During the incubation no further agitation is necessary, although this can be carried out if desired.

After the incubation, the solution optionally can be frozen for storage until further use, e.g. to below −20° C. or more preferable at below −65° C. Ideally, the freezing is carried out as quickly as possible, and the duration of freezing is as short as possible, to preserve the recombinant polypeptide.

Purifying the Recombinant Protein

As discussed above, purifying the recombinant polypeptide in step (iii) is typically performed by carrying out a step of chromatography on the solution. The chromatography may be selected from any suitable chromatography, e.g. immunoaffinity, affinity, hydrophobic interaction, ion exchange, multimodal, size exclusion or metal chelate chromatography.

The step of chromatography may in particular be a step of immunoaffinity chromatography or affinity chromatography. Alternatively, the chromatography step that can be performed as step (iii) is a hydrophobic interaction chromatography step or an ion exchange chromatography step. Moreover, further purification steps may be included in the process after step (iii). For example, one or more hydrophobic interaction chromatography steps may be included in the process. In one embodiment, a hydrophobic interaction chromatography step is carried out on the solution after step (iii), e.g. when step (iii) is an immunoaffinity chromatography step. Similarly, one or more ion exchange chromatography steps may be included in the process. Typically, an ion exchange chromatography step is carried out on the solution after step (iii), particularly when step (iii) is an immunoaffinity or affinity chromatography step. In a preferred embodiment, the immunoaffinity chromatography step is typically followed by a hydrophobic interaction chromatography step (as described above), which is then followed by the ion exchange chromatography step.

Other sequences of steps are also possible. For example, in a first embodiment, a cation exchange chromatography step is carried out on the solution before the step of adding the alkyl glycoside to the solution, step (iii) is then an immunoaffinity chromatography step, and this step is followed by a hydrophobic interaction chromatography step, which is in turn followed by an anion exchange chromatography step. In a second embodiment, an immunoaffinity chromatography step is carried out on the solution before the step of adding the alkyl glycoside to the solution, step (iii) is then an anion exchange chromatography step, and this step is followed by a cation exchange chromatography step. In a third embodiment, an immunoaffinity chromatography step is carried out on the solution before the step of adding the alkyl glycoside to the solution, step (iii) is then a hydrophobic interaction chromatography step, and this step is followed by an anion exchange chromatography step. In a fourth embodiment, a cation exchange chromatography step is carried out on the solution before the step of adding the alkyl glycoside to the solution, step (iii) is then a hydrophobic interaction chromatography step, and this step is followed by an anion exchange chromatography step. Other sequences will be apparent to the skilled person, and can be optimised depending on the recombinant polypeptide of interest. Methods of ion exchange chromatography have been described above. The invention typically uses anion exchange chromatography (e.g. for step (iii) and/or when ion exchange chromatography is used after step (iii)), although cation exchange chromatography may be suitable in some embodiments. An example of using anion exchange chromatography is provided in the modes for carrying out the invention below. The inventors have found that anion exchange chromatography after step (iii) is particularly useful.

Methods of immunoaffinity chromatography and affinity chromatography have similarly been described above. Multimodal, size, metal chelate and hydrophobic interaction chromatography are described below.

Step iii) may optionally include modifying the solution comprising the recombinant polypeptide, e.g. prior to purifying the recombinant polypeptide. The modification may involve altering the solution conductivity and/or including one or more additives. The additive may for example be a chelating agent, e.g. EDTA. The modification may involve dilution or other conditioning of the solution.

Multimodal Chromatography

Multimodal or mixed-mode chromatography is based on media supports that have been functionalized with ligands capable of multiple modes of interaction: ion exchange, hydroxyapatite, affinity, size exclusion, and hydrophobic interactions. The ability to combine these separation methods can enhance selectivity in a polypeptide purification process. There are a number of commercially available mixed-mode media combining different chromatographic elements, in particular based on hydroxyapatite (electrostatic and calcium coordination complexes) or based on hydrophobic ion exchange ligands.

Particular examples of multimodal chromatography materials include Capto MMC Imp Res, Capto MMC ImpAct and Capto adhere (all from GE Healthcare); Toyopearl NH2-750F, Toyopearl MX-Trp-650M (Tosoh); Nuvia cPrime (BioRad) and HEA HyperCel, MEP HyperCel, PPA HyperCel, CMM HyperCel (Pall).

Size Exclusion Chromatography

Size exclusion chromatography (SEC) separates molecules based on their size by filtration through a gel. The gel consists of spherical beads containing pores of a specific size distribution. Separation occurs when molecules of different sizes are included or excluded from the pores within the matrix. Small molecules diffuse into the pores and their flow through the column is retarded according to their size, while large molecules do not enter the pores and are eluted in the column's void volume. Consequently, molecules separate based on their size as they pass through the column and are eluted in order of decreasing molecular weight.

Operating conditions and gel selection depend on the application and the desired resolution. Two common types of separation performed by SEC are fractionation and desalting (or buffer exchange). Fractionation involves separating molecules of varying molecular weights within the gel matrix. The fractionation range of the gel is selected to encompass the molecules of interest. Desalting involves the use of SEC to desalt samples. The molecule of interest is eluted in the void volume, while smaller molecules are retained in the gel pores. To obtain the desired separation, the gel should have an exclusion limit significantly smaller than the molecule of interest.

Particular examples of size exclusion chromatography materials include Bio-Gel P polyacrylamide media.

Metal Chelate Chromatography

Metal chelate chromatography is useful for the purification of histidine-tagged proteins, and can also be used to purify other proteins with exposed histidine, cysteine, and tryptophan residues. Immobilized affinity chromatography (IMAC) resins are used to purify the polypeptide. Highly selective affinities can be achieved depending upon the metal ion used, such as $Cu^{2+}$, $Zn^{2+}$, $Ca^{2+}$, $Co^{2+}$, or $Fe^{3+}$. The binding strength of the target polypeptide to the resin is affected principally by the metal ion and pH of the buffers used. The bound protein can be eluted by competitive elution with imidazole or by lowering the pH.

Hydrophobic Interaction Chromatography

Hydrophobic interaction chromatography (HIC) is generally performed to remove protein aggregates and other process-related impurities. In performing the separation, the sample mixture is contacted with the HIC material, e.g. using a batch purification technique or a column. Prior to the HIC purification it may be desirable to remove any chaotropic agents or very hydrophobic substances, e.g. by passing the mixture through a pre-column.

For example, in the context of batch purification, HIC material is prepared in or equilibrated to the desired equilibration buffer. A slurry of the HIC material is obtained. The solution comprising the recombinant polypeptide is contacted with the slurry to adsorb the polypeptide to be separated to the HIC material. The solution comprising the impurities that do not bind to the HIC material is separated from the slurry, e.g. by allowing the slurry to settle and removing the supernatant. The slurry can be subjected to one or more washing steps. If desired, the slurry can be contacted with a solution of lower conductivity to desorb polypeptide that has bound to the HIC material. In order to elute bound polypeptide, the salt concentration can be decreased.

Whereas ion exchange chromatography relies on the charges of the polypeptide to isolate it, hydrophobic interaction chromatography uses the hydrophobic properties of the polypeptide. Hydrophobic groups on the polypeptide interact with hydrophobic groups on the column. The more hydrophobic a polypeptide is the stronger it will interact with the column. Thus the HIC step e.g. removes host cell derived impurities and sometimes product-related impurities.

Adsorption of the polypeptide to a HIC column is favoured by high salt concentrations, but the actual concentrations can vary over a wide range depending on the nature of the polypeptide and the particular HIC ligand chosen. HIC columns normally comprise a base matrix (e.g. crosslinked agarose or synthetic copolymer material) to which hydrobobic ligands (e.g. alkyl or aryl groups) are coupled. A suitable HIC column comprises an agarose resin substituted with phenyl groups (e.g. a Phenyl Sepharose™ column). Many HIC columns are available commercially. Examples include, but are not limited to, Phenyl Sepharose™ 6 Fast Flow column with low or high substitution (GE Healthcare Life Sciences); Phenyl Sepharose™ High Performance column (GE Healthcare Life Sciences); Octyl Sepharose™ High Performance column or Butyl Sepharose Fast Flow or High Performance column (GE Healthcare Life Sciences); Fractogel™ EMD Propyl or Fractogel™ EMD Phenyl columns (E. Merck, Germany); Macro-Prep™ Methyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, PA).

An example of using HIC is provided in the modes for carrying out the invention below. The inventors have found that HIC chromatography after step (iii) is particularly useful, e.g. with a Butyl Sepharose™ High Performance column (GE Healthcare Life Sciences).

Further Treatment of the Solution Comprising the Recombinant Polypeptide

The solution may undergo further treatment after step (iii) and any additional purification steps as described above.

For example, a step of viral filtration may be carried out. In certain aspects of the invention, the solution comprising the recombinant polypeptide from the preceding step is subjected to filtration for the removal of viral particles, including intact viruses, if present. A non-limiting example of a suitable filter is the Ultipor DV50™ filter from Pall Corporation or the Planova 20N filter from Asahi Kasei Medical Co., Ltd. Other viral filters can be used in this filtration step and are well known to those skilled in the art. In certain embodiments, following the filtration process, the filter is washed using e.g. the elution buffer used in the preceding step, in order to remove any recombinant polypeptide retained in the filter housing.

One or more steps of ultrafiltration and/or diafiltration may also be used to purify the recombinant polypeptide. These steps may concentrate the recombinant polypeptide and/or exchange its buffer. Typically, the one or more ultrafiltration and/or diafiltration steps are performed after the above viral filtration step.

Ultrafiltration is described in detail in refs. 8 and 9. One filtration process is Tangential Flow Filtration as described in ref. 10. Ultrafiltration is generally considered to mean filtration using filters with a pore size of smaller than 0.1 μm. By employing filters having such small pore size, the volume of the sample can be reduced through permeation of the sample buffer through the filter while the recombinant polypeptide is retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained polypeptide. In certain embodiments of the present invention, a diafiltration step is employed to exchange the various buffers used in connection with the process of the invention, optionally prior to further purification steps, as well as to remove impurities from the recombinant polypeptide.

Pharmaceutical Compositions and Methods

Pharmaceutical compositions of the invention can be prepared for storage as lyophilized formulations or aqueous solutions by mixing a purified recombinant polypeptide of the invention with optional pharmaceutically-acceptable carriers, excipients or stabilizers typically employed in the art (all of which are referred to herein as "carriers"), i.e. buffering agents, stabilizing agents, preservatives, isotonifiers, non-ionic detergents, antioxidants, and other miscellaneous additives (see ref. 11). Such additives must be non-toxic to the recipients at the dosages and concentrations employed.

A pharmaceutical composition of the invention can also contain a second therapeutic agent in addition to the purified recombinant polypeptide of the invention.

The compositions may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 12].

The pharmaceutical composition is typically sterile. It is preferably pyrogen-free.

In many embodiments, the composition is buffered e.g. at between pH 6 and pH 8, generally around pH 7. The composition may be aqueous, or it may be lyophilised.

The invention also provides a delivery device containing a pharmaceutical composition of the invention. The device may be, for example, a syringe or an inhaler.

Once formulated, the compositions of the invention can be administered directly to a subject. The subjects to be treated can be animals; in particular, human subjects can be treated.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the steps are carried out in the indicated order, i.e. in numerical or alphabetical order. However, the skilled person will understand that the order of steps may be altered while still achieving useful results. The invention can also provide a process involving less than the total number of steps. For example, if a solution comprising the recombinant protein has already been purified by carrying out a step of ion exchange chromatography on the solution then this step can be omitted from the processes of the invention. Similarly, a step of adding an alkyl glycoside to the solution comprising the recombinant polypeptide can be carried out to give material ready for step (iii), but step (iii) need not be performed. Step (iii) need not be performed in order to fall within the scope of the invention, as the pre-treated material has utility as an intermediate for subsequent purification, and may be used, stored, exported, etc. for later use e.g. for immunoaffinity chromatography or chromatography in general. These different steps can be performed at different times by different people in different places (e.g. in different countries).

BRIEF DESCRIPTION OF DRAWINGS

FIG. 8 shows the PRV inactivation capacity of a variety of alkyl glycosides: open square show PRV inactivation in 11.9 mg/ml D'D3-FP at 60 mM OG, open triangle show PRV inactivation in 11.9 mg/ml D'D3-FP at 60 mM n-Decyl-ß-D-glucopyranoside, open rhomb show PRV inactivation in 11.9 mg/ml D'D3-FP at 60 mM n-Octyl-ß-D-maltoside, closed square show PRV inactivation in 11.9 mg/ml D'D3-FP at 60 mM n-Dodecyl-ß-D-maltoside, closed triangle show PRV inactivation in 11.9 mg/ml D'D3-FP at 60 mM n-Dodecyl-ß-D-glucopyranoside, closed rhomb show PRV inactivation in 11.9 mg/ml D'D3-FP at 60 mM n-Decyl-ß-D-maltoside.

FIG. 12 shows VSV inactivation by SD treatment compared to OG: closed triangle show VSV inactivation by 40 mM OG in 10.4 mg/ml D'D3-FP at 24.5° C. and open square show VSV inactivation by 1% PS80+0.3% TNBP in 10.4 mg/ml D'D3-FP at 26.5° C.

FIG. 13 shows Vaccinia virus inactivation by SD treatment compared to OG: closed triangle show Vaccinia virus inactivation by 40 mM OG in 10.4 mg/ml D'D3-FP at 24.5° C. and open square show Vaccinia virus inactivation by 1% PS80+0.3% TNBP in 10.4 mg/ml D'D3-FP at 26.5° C.

MODES FOR CARRYING OUT THE INVENTION

Example 1

Comparison of n-octyl-beta-D-glucopyranoside with a Solvent/Detergent Mixture and Buffer as a Control

SUMMARY

Treatment of recombinant D'D3-FP (ref. 7) with a typical solvent/detergent mixture of polysorbate 80 and tri-n-butylphosphate (PS80/TNBP) was compared with treatment with the alkyl glycoside, n-octyl-β-D-glucopyranoside (OG). Initial experiments showed that the rD'D3-FP remained stable upon treatment with the alkyl glycoside. Importantly, rapid inactivation of three model viruses was observed with the alkyl glycoside even in the absence of the tri-n-butylphoshate (TNBP). Virus inactivation was complete within one hour at temperatures as low as 5° C., with or without agitation. The efficient procedure tolerated the use of an unexpectedly wide range of process parameters resulting in efficient virus inactivation (the tested range for OG was 4-25° C., for less than or equal to 30 minutes (typically 120 min were followed up) at concentrations of more than or equal to 20 mM). Unexpectedly, the presence of the alkyl glycoside in the feedstream of a subsequent chromatography purification step resulted in significantly lower host cell DNA and host cell protein levels at the eluate stage in comparison to the use of the PS80/TNBP or control buffer solutions.

Methods and Results rD'D3-FP contains the FVIII binding site of the von-Willebrand-Factor (vWF) protein generated by recombinant DNA technology. The rD'D3-FP cDNA sequence was transfected into Chinese Hamster Ovary (CHO) cells and the polypeptide was expressed to perform the investigations described. Laboratory studies were conducted to assess the virus inactivation capacity of the alkyl glycoside step with a range of representative virus models. The use of the retrovirus MuLV (murine leukemia virus) as a relevant virus is particularly relevant for CHO cell derived products as these are known to contain endogenous retrovirus-like particles. The flavivirus BVDV (bovine viral diarrhea virus) and the herpesvirus PRV (pseudorabies virus) which is in general more stable to S/D treatment were used in virus evaluation studies to demonstrate the broad virus inactivation capacity of the alkyl glycoside treatment.

The virus titres of all samples studied were determined using end point dilution assays immediately after generating the sample and were calculated according to the Spearman-Kärber method as given in Ref 13.

For these OG studies two process control parameters were chosen to test challenge conditions concerning virus inactivation: 1) an OG detergent concentration of 20 mM; and 2) a temperature of 6° C.±1° C. Samples of a rD. D3-FP intermediate (protein concentration of about 14 mg/ml) were diluted appropriately or used undiluted and spiked with virus to be studied resulting in the desired detergent concentration.

Samples were taken before the addition of detergent (untreated) and at different time-points after the addition of detergent. The samples were assayed immediately by diluting 1:100 in cell culture medium to stop the reaction and to render the samples non-toxic in the virus assays.

The following reduction factors were obtained (which for all viruses were limited only by the test system, in particular the detection limit as well as the amount of virus used for spiking):

TABLE 1

| Virus Studied | LRV [$\log_{10}$] | Condition studied | After incubation for | Kinetic given in | Data given in |
|---|---|---|---|---|---|
| MuLV | ≥4.2 | 20 mM OG at 6° C. | 15 minutes | FIG. 1 | Table 2 |
| BVDV | ≥5.3 | | 15 minutes | FIG. 2 | Table 3 |
| PRV | ≥6.3 | | 60 minutes | FIG. 3 | Table 4 |

The virus hold control results in FIGS. 1-3 (Tables 2-4, respectively) indicated that there was no significant reduction in the virus stability sample over the incubation period which confirms that the reduction demonstrated was due to the action of the alkyl glycoside detergent treatment. Additionally, the figures demonstrate that the virus inactivation was very rapid and in all cases greater than 4 logs of virus inactivation was observed. MuLV and BVDV were completely inactivated at a temperature of 6° C.±1° C. by an OG detergent concentration of 20 mM by the first studied 15 minutes time point while complete PRV inactivation took 60 minutes.

TABLE 2

MuLV Inactivation by e.g. OG

| time in minutes | MuLV, 4.4 mg/ml rD'D3-FP, 200 mM OG + 0.3% TNBP at 21° C., with agitation | held control | MuLV, 8.4 mg/ml rD'D3-FP, 20 mM OG at 6° C. without agitation | held control |
|---|---|---|---|---|
| prior OG addition | 6.2 | 6.2 | 5.4 | 5.4 |
| 15 | n.d. | n.d. | ≤1.2 | n.d. |
| 30 | ≤2.7 | n.d. | ≤1.2 | n.d. |
| 60 | ≤1.7 | n.d. | ≤1.2 | n.d. |
| 120 | ≤1.7 | 4.8 | ≤1.2 | 5.2 |

TABLE 3

BVDV Inactivation by e.g. OG

| time in minutes | BVDV, 4.4 mg/ml rD'D3-FP, 200 mM OG + 0.3% TNBP at 21° C., with agitation | held control | BVDV, 8.4 mg/ml rD'D3-FP, 20 mM OG at 6° C. without agitation | held control |
|---|---|---|---|---|
| prior OG add | 6.5 | 6.5 | 6.5 | 6.5 |
| 15 | n.d. | n.d. | ≤1.2 | n.d. |
| 30 | ≤2.7 | n.d. | ≤1.2 | n.d. |
| 60 | ≤1.7 | n.d. | ≤1.2 | 6.4 |
| 120 | ≤1.7 | 6.4 | n.d. | n.d. |

TABLE 4

PRV Inactivation at e.g. 20 mM OG at 6° C.

| time in minutes | PRV, 4.4 mg/ml D'D3-FP, 200 mM OG + 0.3% TNBP at 21° C., shaken | held control 16070521 | PRV, 8.4 mg/ml D'D3-FP, 20 mM OG at 6° C. without agitation | held control 16111422 |
|---|---|---|---|---|
| prior OG add | 8.4 | 8.4 | 7.8 | 7.8 |
| 15 | n.d. | n.d. | 1.5 | n.d. |
| 30 | ≤2.7 | n.d. | 1.3 | n.d. |
| 60 | ≤1.7 | n.d. | ≤1.2 | 7.6 |
| 120 | ≤1.7 | 8.0 | n.d. | n.d. |

Figure 1:
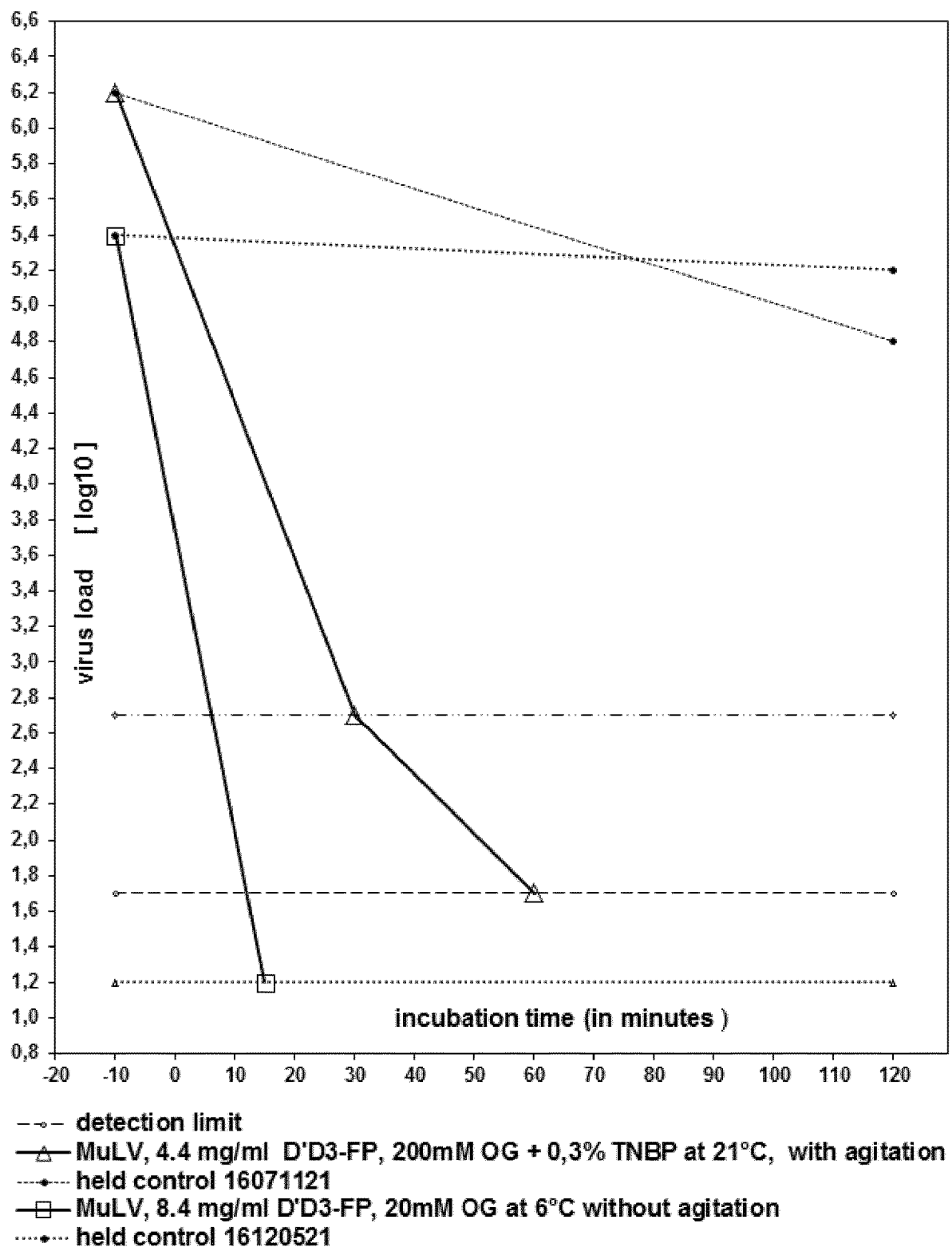
FIG. 1 shows MuLV inactivation with OG/TNBP and with OG only: open triangle show MuLV inactivation in 4.4 mg/ml D'D3-FP with 200 mM OG+0.3% TNBP at 21° C. under agitation, open square show MuLV inactivation in 8.4 mg/ml D'D3-FP with 20 mM OG at 6° C. without agitation.
Figure 2:
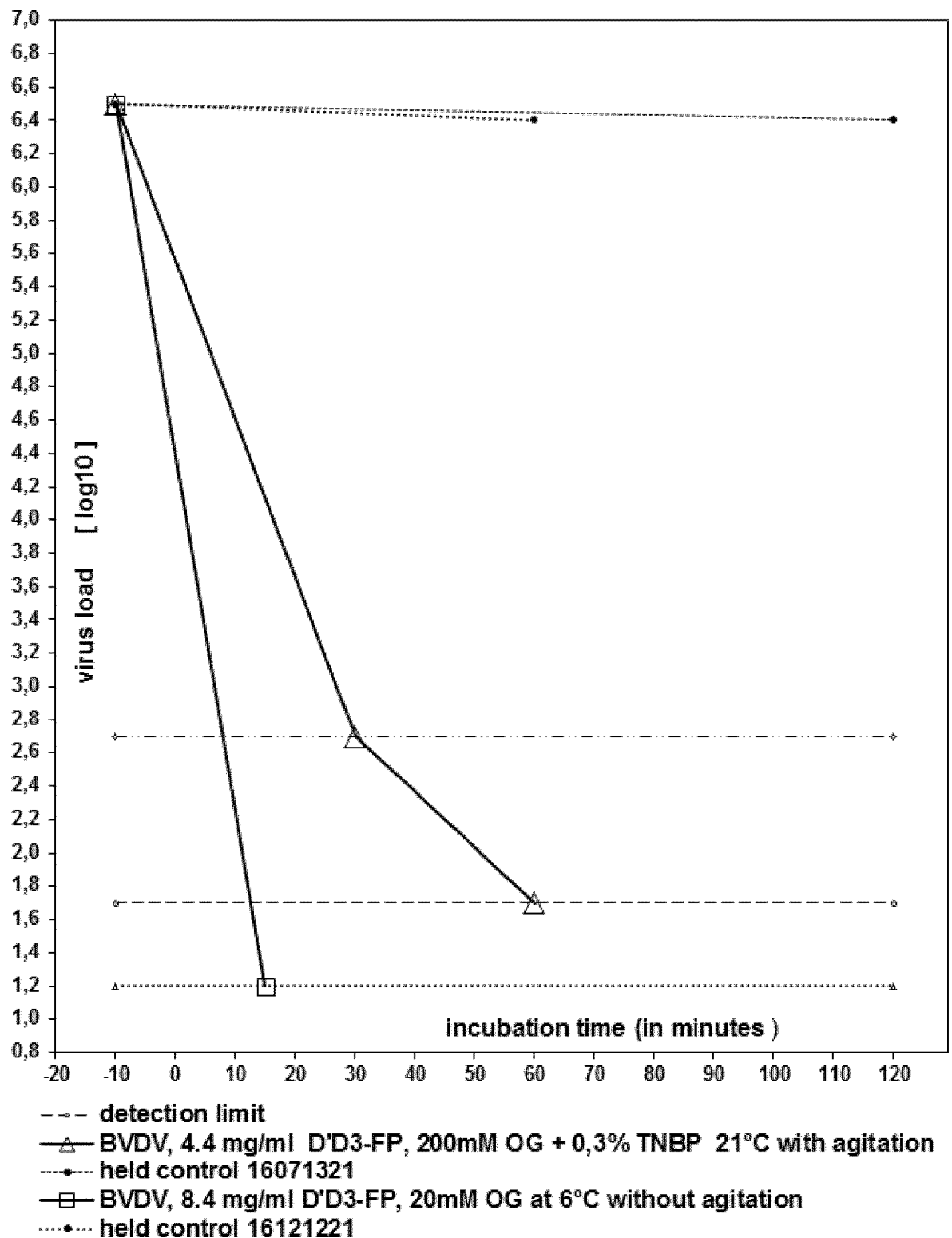
FIG. 2 shows BVDV inactivation with OG/TNBP and with OG only: open triangle show BVDV inactivation in 4.4 mg/ml D'D3-FP with 200 mM OG+0.3% TNBP 21° C. under agitation, open square show BVDV inactivation in 8.4 mg/ml D'D3-FP with 20 mM OG at 6° C. without agitation.
Figure 3:
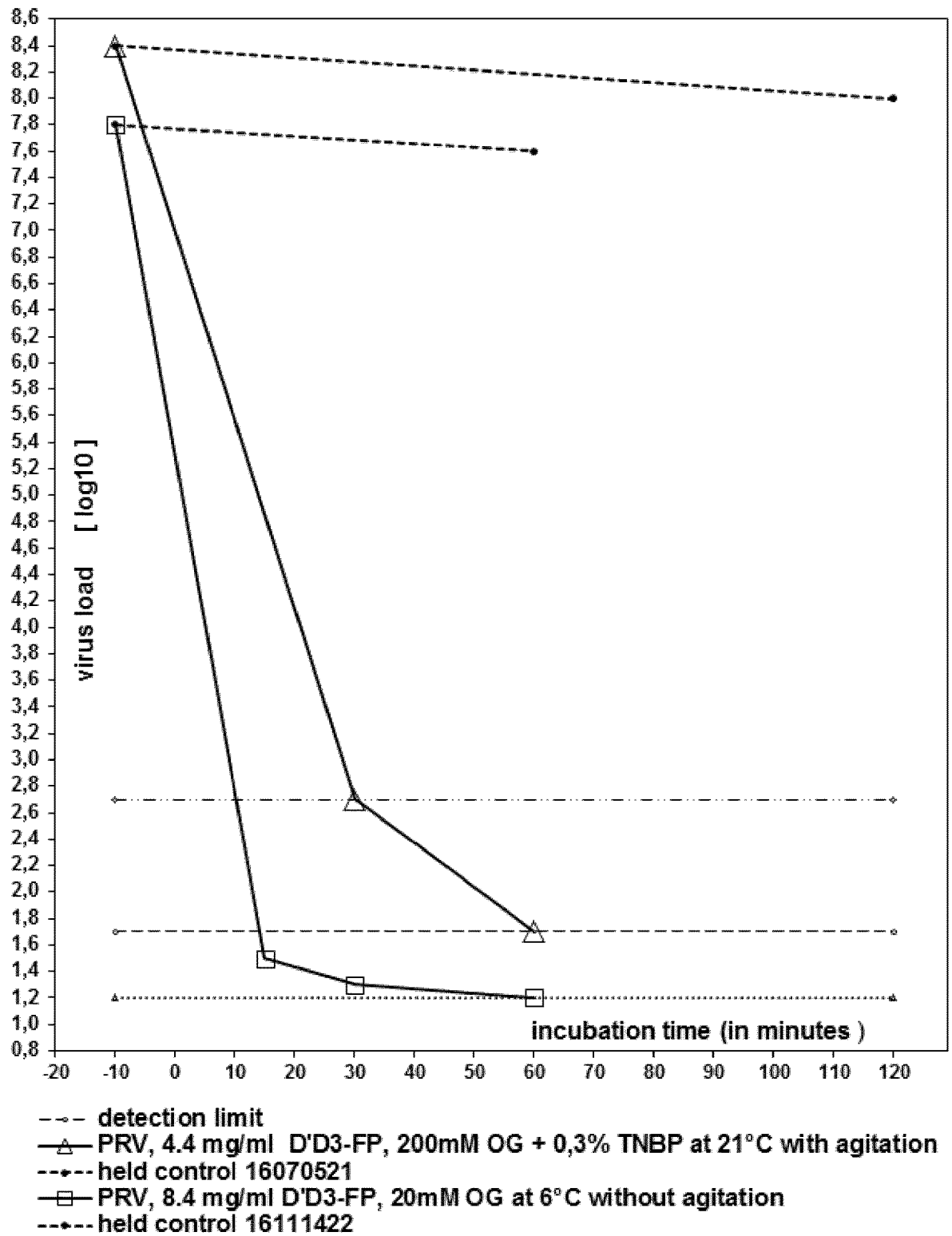
FIG. 3 shows PRV inactivation with OG/TNBP and with OG only: open triangle show PRV inactivation in 4.4 mg/ml D'D3-FP with 200 mM OG+0.3% TNBP at 21° C., with agitation, open square show PRV inactivation in 8.4 mg/ml D'D3-FP with 20 mM OG at 6° C. without agitation.

In additional robustness studies with PRV, a more resistant enveloped virus, the following parameters were studied:

Variation of protein concentration had no influence of the PRV inactivation (FIG. 3, Table 4).

Figure 4:
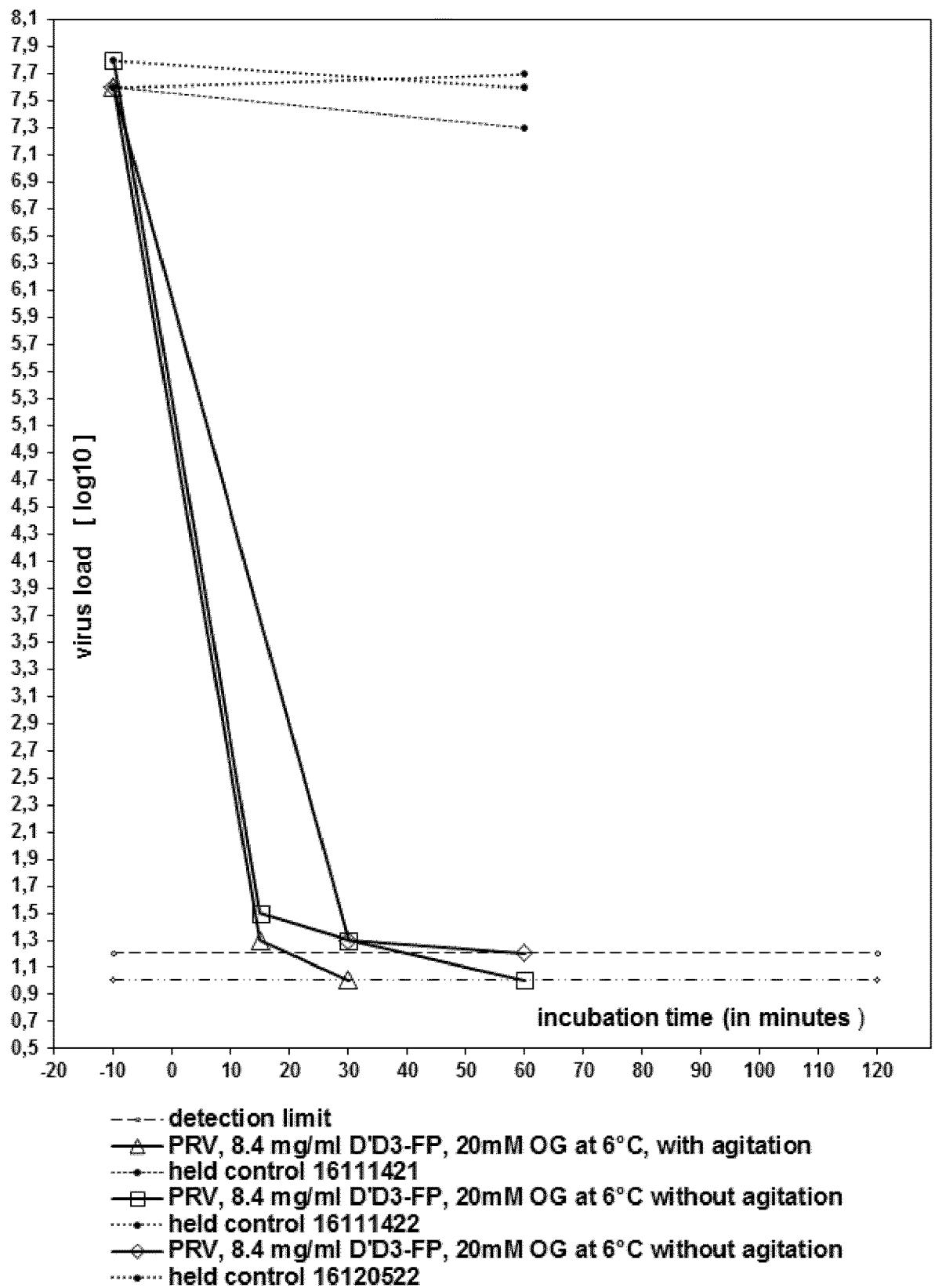
FIG. 4 shows PRV inactivation with OG at 6° C., either with agitation or without agitation: open triangle show PRV inactivation in 8.4 mg/ml D'D3-FP with 20 mM OG at 6° C. under agitation, open square show PRV inactivation in 8.4 mg/ml D'D3-FP with 20 mM OG at 6° C. without agitation, open rhomb show PRV inactivation in 8.4 mg/ml D'D3-FP with 20 mM OG at 6° C. without agitation.

Agitation during the 20 mM OG incubation at 6° C. resulted in slightly faster PRV inactivation (FIG. 4, Table 5). Nevertheless, PRV was completely and reliably inactivated by 20 mM OG treatment without any agitation during OG incubation.

Figure 5:
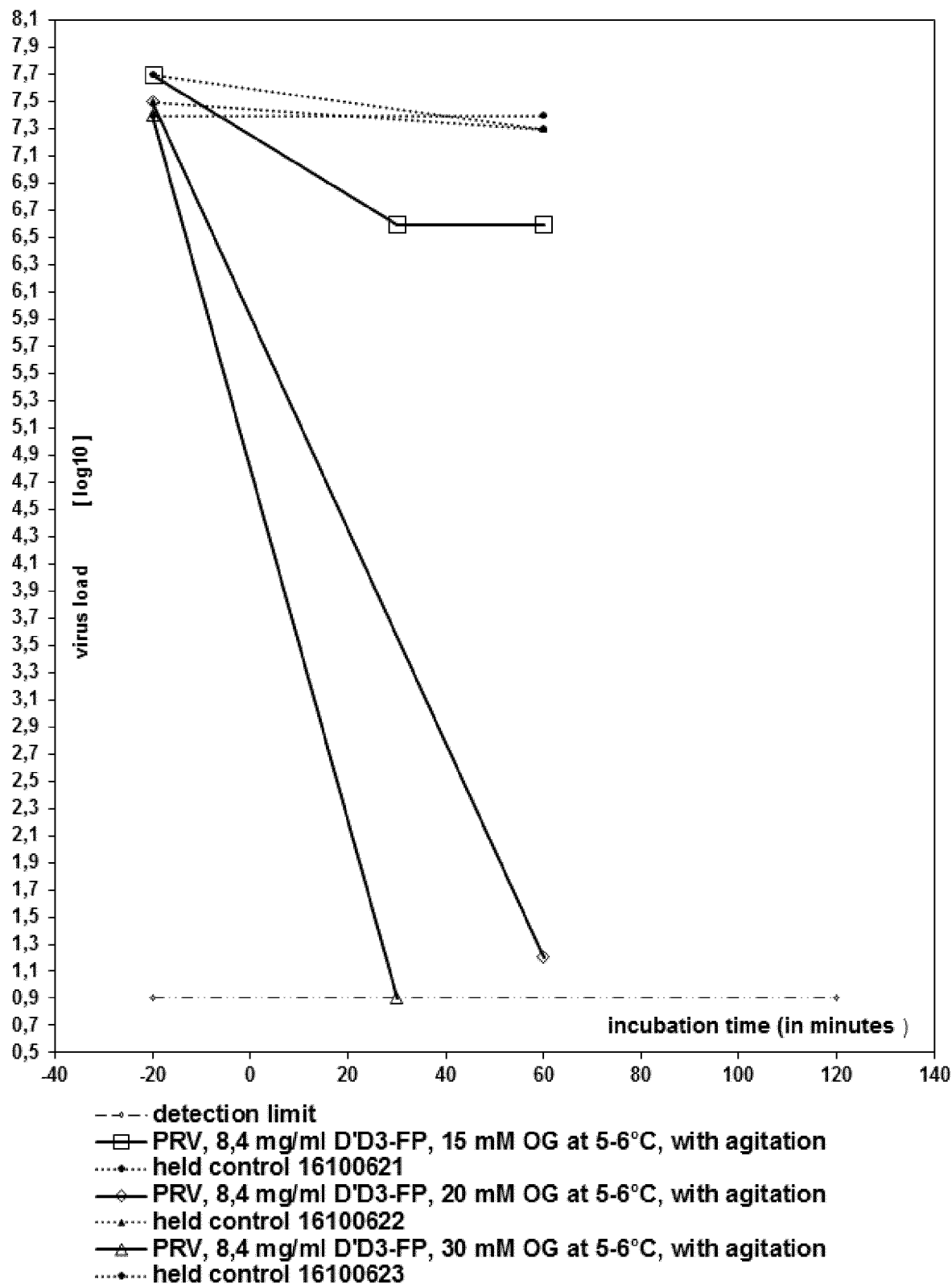
FIG. 5 shows PRV inactivation with different concentrations of OG at 5-6° C. with agitation: open square show PRV inactivation in 8.4 mg/ml D'D3-FP with 15 mM OG at 5-6° C. under agitation, open rhomb show PRV inactivation in 8.4 mg/ml D'D3-FP with 20 mM OG at 5-6° C. under agitation, open triangle show PRV inactivation in 8.4 mg/ml D'D3-FP with 30 mM OG at 5-6° C. under agitation.

Lowering the OG concentration to 15 mM (below CMC) at 6° C. resulted in no significant PRV inactivation (FIG. 5, Table 6).

Figure 6:
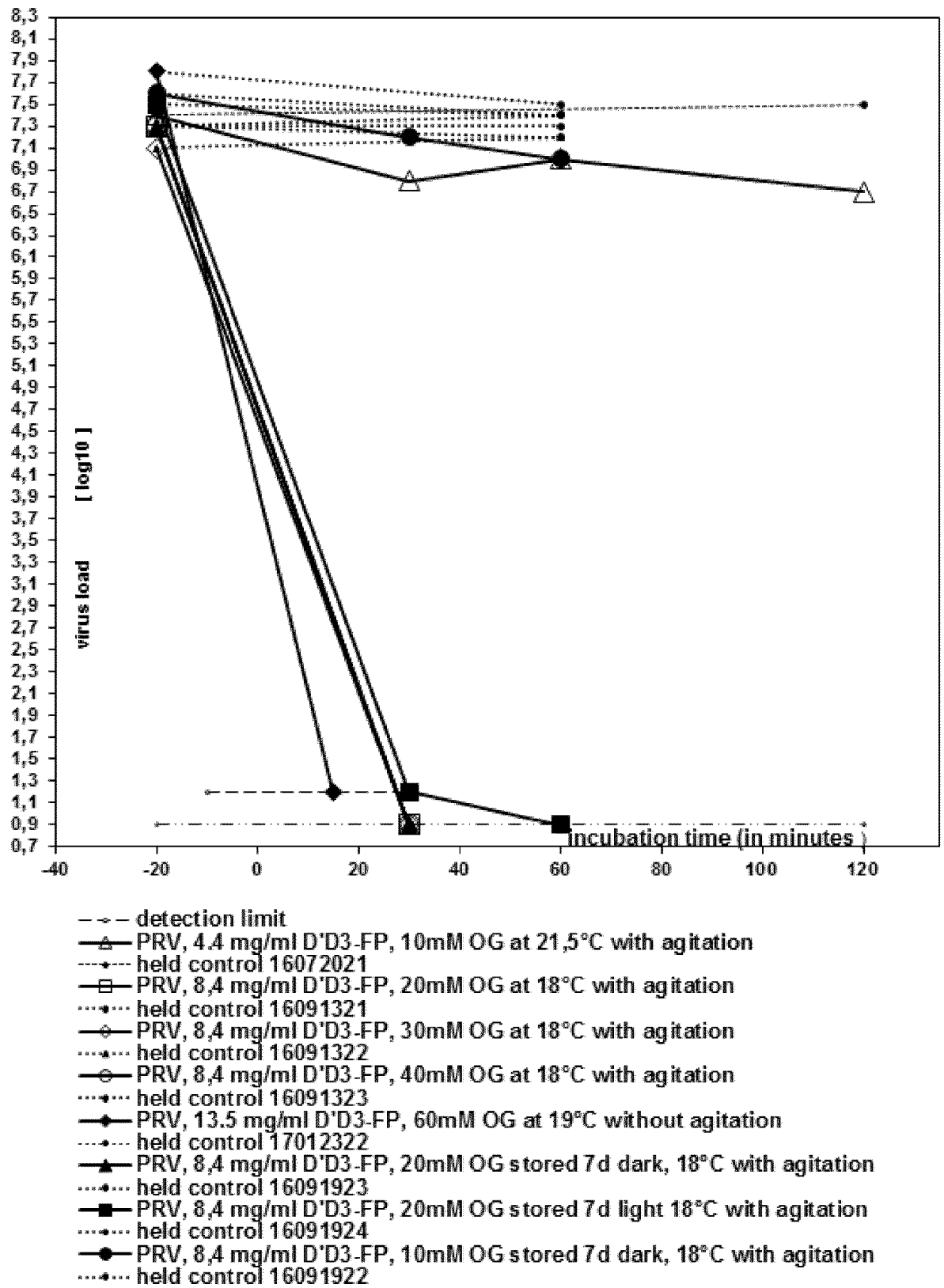
FIG. 6 shows PRV inactivation with various concentrations of OG at 18-19° C.: open triangle show PRV inactivation in 4.4 mg/ml D'D3-FP with 10 mM OG at 21.5° C. under agitation, open square show PRV inactivation in 8.4 mg/ml D'D3-FP with 20 mM OG at 18° C. under agitation, open rhomb show PRV inactivation in 8.4 mg/ml D'D3-FP with 30 mM OG at 18° C. under agitation, open circle show PRV inactivation in 8.4 mg/ml D'D3-FP with 40 mM OG at 18° C. under agitation, closed rhomb show PRV inactivation in 13.5 mg/ml D'D3-FP with 60 mM OG at 19° C. under agitation, closed triangle show PRV inactivation in 8.4 mg/ml D'D3-FP with 20 mM OG stored 7d dark at 18° C. under agitation, closed square show PRV inactivation in 8.4 mg/ml D'D3-FP with 20 mM OG stored 7d light at 18° C. under agitation, closed circle show PRV inactivation in 8.4 mg/ml D'D3-FP with 10 mM OG stored 7d dark at 18° C. under agitation.

A similar observation was made at 10 mM OG at 21° C. (FIG. 6, Table 7). Increasing the OG concentration to 30 mM or higher resulted in fast PRV inactivation. Furthermore, storage of the OG stock solution for 7 days (in the dark) had no influence on the inactivation capacity.

Figure 7:
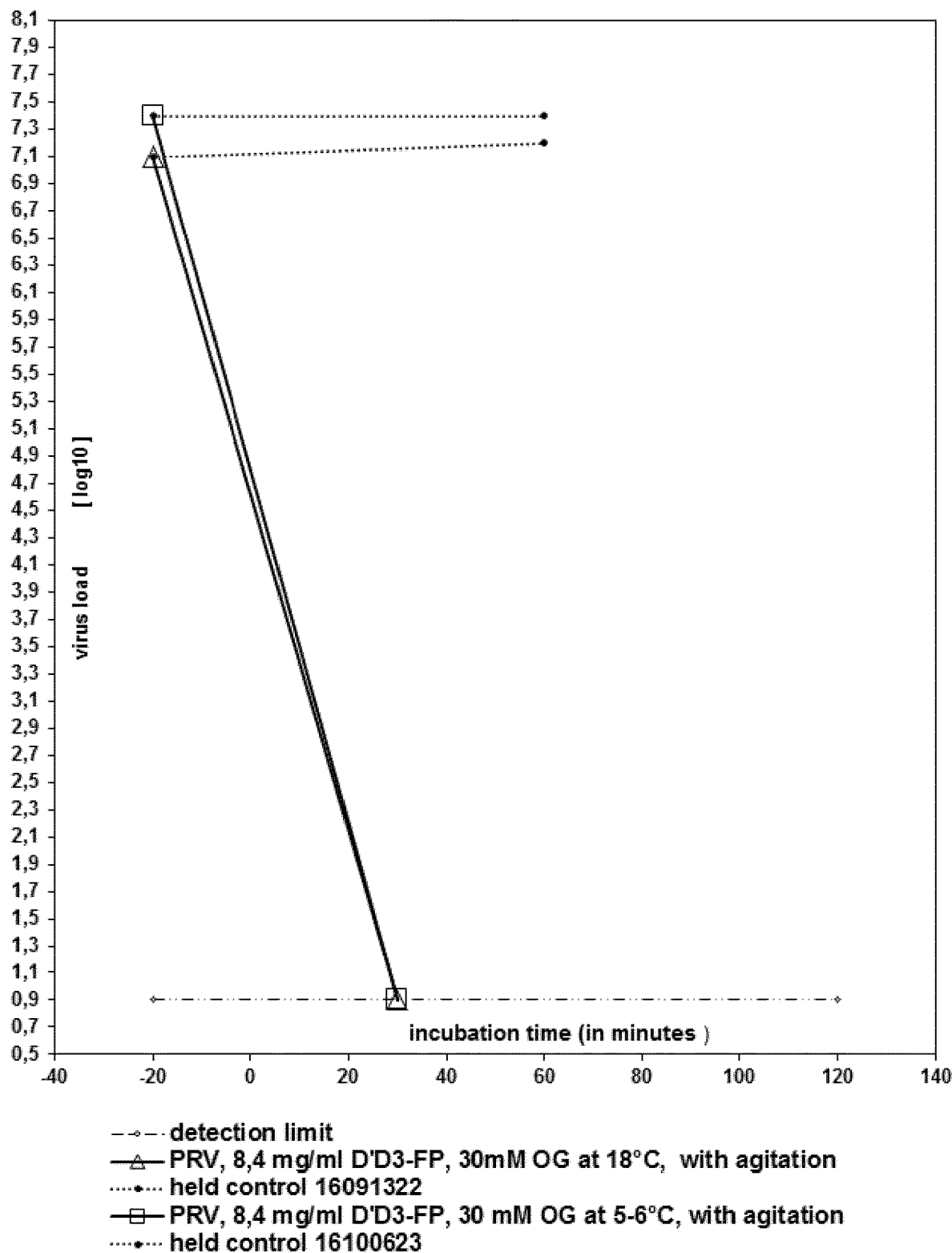
FIG. 7 shows PRV inactivation with equal mM concentrations of OG at 18 or 5-6° C.: open triangle show PRV inactivation in 8.4 mg/ml D'D3-FP with 30 mM OG at 18° C. under agitation, open square show PRV inactivation in 8.4 mg/ml D'D3-FP with 30 mM OG at 5-6° C. under agitation.
Figure 9:
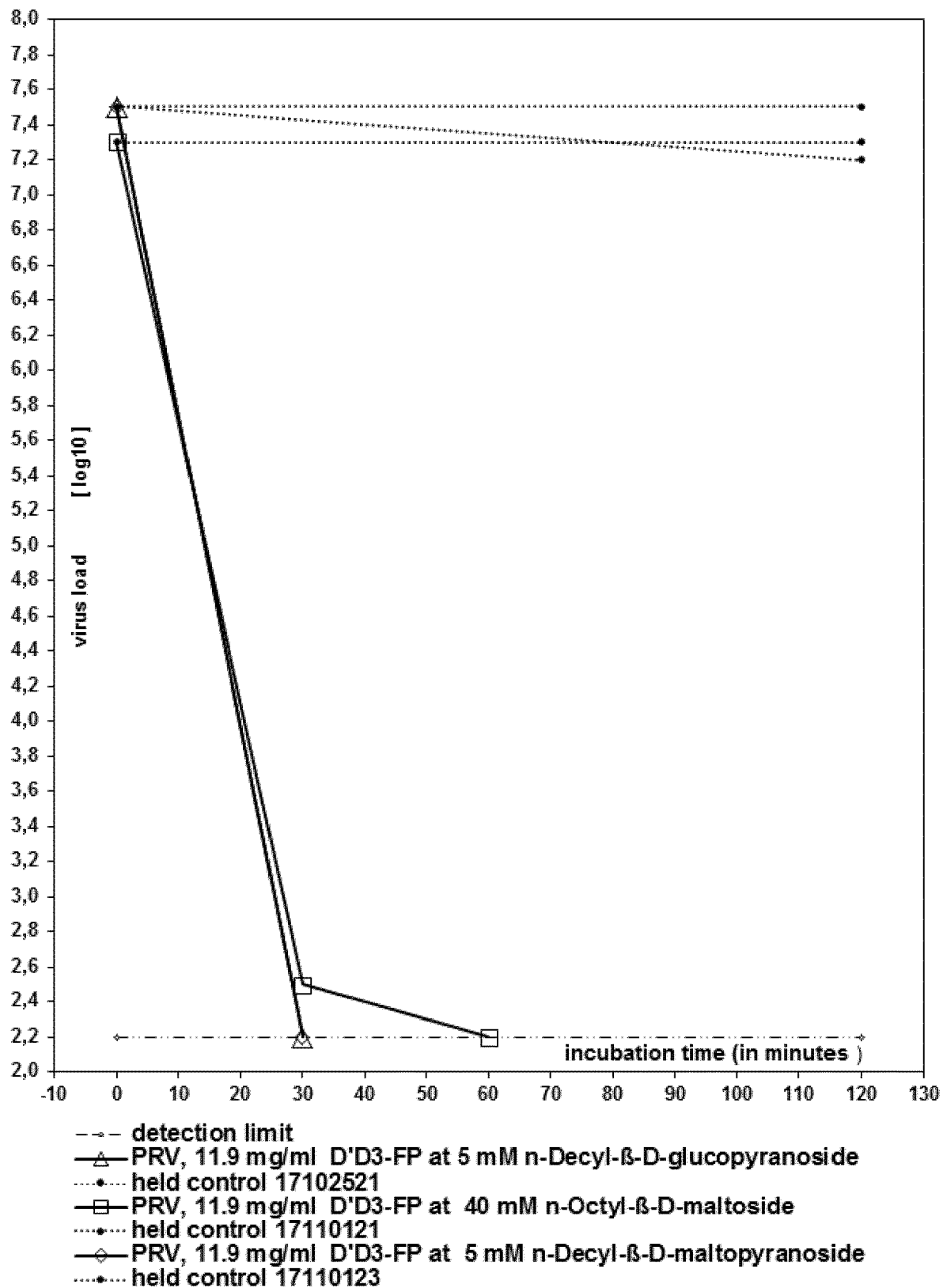
FIG. 9 shows the PRV inactivation capacity of n-decyl-ß-D-glucopyranoside, n-decyl-ß-D-maltoside and n-octyl-ß-D-maltoside at lower concentrations (about twice as high as their CMC values): open triangle show PRV inactivation in 11.9 mg/ml D'D3-FP at 5 mM n-Decyl-R-D-glucopyranoside, open square show PRV inactivation in 11.9 mg/ml D'D3-FP at 40 mM n-Octyl-ß-D-maltoside, open rhomb show PRV inactivation in 11.9 mg/ml D'D3-FP at 5 mM n-Decyl-ß-D-maltoside.

Increasing the incubation temperature from 6° C. to 18° C. at 30 mM OG resulted in no faster PRV inactivation (FIG. 7, Table 8). 60 mM of several other alkyl glycosides completely inactivates PRV very fast (FIG. 8, Table 9). Especially, low amounts of alkyl glycosides (about twice as high as the CMC) completely inactivates PRV very fast (FIG. 9, Table 10a).

TABLE 5

PRV Inactivation at 20 mM OG by with agitation or not at 6° C.

| time in minutes | PRV, 8.4 mg/ml rD'D3-FP, 20 mM OG at 6° C., with agitation | held control | PRV, 8.4 mg/ml rD'D3-FP, 20 mM OG at 6° C. without agitation | held control | PRV, 8.4 mg/ml rD'D3-FP, 20 mM OG at 6° C. without agitation | held control |
|---|---|---|---|---|---|---|
| prior OG add | 7.6 | 7.6 | 7.8 | 7.8 | 7.6 | 7.6 |
| 15 | 1.3 | n.d. | 1.5 | n.d. | n.d. | n.d. |
| 30 | ≤1.0 | n.d. | 1.3 | n.d. | 1.3 | n.d. |
| 60 | ≤1.0 | 7.3 | ≤1.0 | 7.6 | ≤1.2 | 7.7 |

TABLE 6

PRV Inactivation at various mM OG at 6° C.

| time in minutes | PRV, rD'D3-FP 8.4 mg/ml, 15 mM OG at 5-6° C., with agitation | held control | PRV, rD'D3-FP 8.4 mg/ml, 20 mM OG at 5-6° C., with agitation | held control | PRV, rD'D3-FP 8.4 mg/ml, 30 mM OG at 5-6° C., with agitation | held control |
|---|---|---|---|---|---|---|
| prior OG add | 7.7 | 7.7 | 7.5 | 7.5 | 7.4 | 7.4 |
| 30 | 6.6 | n.d. | n.d. | n.d. | ≤0.9 | n.d. |
| 60 | 6.6 | 7.3 | 1.2 | 7.3 | ≤0.9 | 7.4 |

TABLE 7

PRV Load in log10 at various mM OG at 18-22° C.

| time in min | PRV, rD'D3-FP 4.4 mg/ml, 10 mM OG at 21.5° C., with agitation | held control | PRV, rD'D3-FP 8.4 mg/ml, 20 mM OG at 18° C., with agitation | held control | PRV, rD'D3-FP 8.4 mg/ml, 30 mM OG at 18° C., with agitation | held control | PRV, rD'D3-FP 8.4 mg/ml, 40 mM OG at 18° C., with agitation | held control |
|---|---|---|---|---|---|---|---|---|
| prior OG add | 7.4 | 7.4 | 7.3 | 7.3 | 7.1 | 7.1 | 7.3 | 7.3 |
| 15 | n.d. | n.d. | n.d. | n.d. | n.d. | n.d. | n.d. | n.d. |
| 30 | 6.8 | n.d. | ≤0.9 | n.d. | ≤0.9 | n.d. | ≤0.9 | n.d. |
| 60 | 7.0 | n.d. | ≤0.9 | 7.3 | ≤0.9 | 7.2 | ≤0.9 | 7.2 |
| 120 | 6.7 | 7.5 | n.d. | n.d. | n.d. | n.d. | n.d. | n.d. |

| time in min | PRV, 13.5 mg/ml rD'D3-FP, 60 mM OG at 19° C. without agitation | held control | PRV, rD'D3-FP 8.4 mg/ml, 20 mM OG stored 7 d dark, at 18° C., with agitation | held control | PRV, rD'D3-FP 8.4 mg/ml, 20 mM OG stored 7 d light at 18° C., with agitation | held control | PRV, rD'D3-FP 8.4 mg/ml, 10 mM OG stored 7 d dark, at 18° C., with agitation | held control |
|---|---|---|---|---|---|---|---|---|
| prior OG add | 7.8 | 7.8 | 7.3 | 7.3 | 7.5 | 7.5 | 7.6 | 7.6 |
| 15 | ≤1.2 | n.d. | n.d. | n.d. | n.d. | n.d. | n.d. | n.d. |
| 30 | ≤1.2 | n.d. | ≤0.9 | n.d. | 1.2 | n.d. | 7.2 | n.d. |
| 60 | ≤1.2 | 7.5 | ≤0.9 | 7.4 | ≤0.9 | 7.4 | 7.0 | 7.4 |
| 120 | n.d. | n.d. | n.d. | n.d. | n.d. | n.d. | n.d. | n.d. |

TABLE 8

PRV Inactivation at 30 mM OG at 6° C. or 18° C.

| prior OG add | PRV, rD'D3-FP 8.4 mg/ml, 30 mM OG at 18° C., with agitation | held control | PRV, rD'D3-FP 8.4 mg/ml, 30 mM OG at 5-6° C., with agitation | held control |
|---|---|---|---|---|
| 0 | 7.1 | 7.1 | 7.4 | 7.4 |
| 30 | ≤0.9 | n.d. | ≤0.9 | n.d. |
| 60 | ≤0.9 | 7.2 | ≤0.9 | 7.4 |

TABLE 9

PRV inactivation capacity of a variety of alkyl glycosides

| time in minutes | PRV, 60 mM OG | held control | PRV, 60 mM n-Decyl-β-D-glucopyranoside | held control | PRV, 60 mM n-Octyl-β-D-maltoside | held control |
|---|---|---|---|---|---|---|
| prior add | 7.8 | 7.8 | 7.5 | 7.5 | 7.6 | 7.6 |
| 30 | ≤2.2 | n.d. | ≤2.2 | n.d. | 2.5 | n.d. |
| 60 | ≤2.2 | n.d. | ≤2.2 | n.d. | ≤2.2 | n.d. |
| 120 | ≤2.2 | 7.6 | ≤2.2 | 7.5 | ≤2.2 | 7.6 |

| time in minutes | PRV, 60 mM n-Dodecyl-β-D-maltoside | held control | PRV, 60 mM n-Dodecyl-β-D-glucopyranoside | held control | PRV, 60 mM n-Decyl-β-D-maltopyranoside | held control |
|---|---|---|---|---|---|---|
| prior add | 7.8 | 7.8 | 7.7 | 7.7 | 7.6 | 7.6 |
| 30 | ≤4.2 | n.d. | ≤2.2 | n.d. | ≤2.2 | n.d. |
| 60 | ≤4.2 | n.d. | ≤2.2 | n.d. | ≤2.2 | n.d. |
| 120 | ≤4.2 | 7.5 | ≤2.2 | 7.5 | ≤2.2 | 7.5 |

TABLE 10a

PRV inactivation capacity of n-decyl-β-D-glucopyranoside, n-decyl-β-D-maltoside and n-octyl-β-D-maltoside at lower concentrations (about twice as high as their CMC values)

| time in minutes | PRV, 5 mM n-Decyl-β-D-glucopyranoside | held control | PRV, 40 mM n-Octyl-β-D-maltoside | held control | PRV, 5 mM n-Decyl-β-D-maltoside | held control |
|---|---|---|---|---|---|---|
| prior add | 7.5 | 7.5 | 7.3 | 7.3 | 7.5 | 7.5 |
| 30 | ≤2.2 | n.d. | 2.5 | n.d. | ≤2.2 | n.d. |
| 60 | ≤2.2 | n.d. | ≤2.2 | n.d. | ≤2.2 | n.d. |
| 120 | ≤2.2 | 7.5 | ≤2.2 | 7.3 | ≤2.2 | 7.2 |

Under all robustness conditions evaluated the kinetics of virus inactivation were similar to the standard conditions. Overall, the OG treatment step was shown to be effective and robust and to have a high capacity to inactivate enveloped viruses, including the particularly relevant retrovirus MuLV. Also for other alkyl glycosides their capacity to effectively inactivate relevant viruses could be shown.

Figure 12:
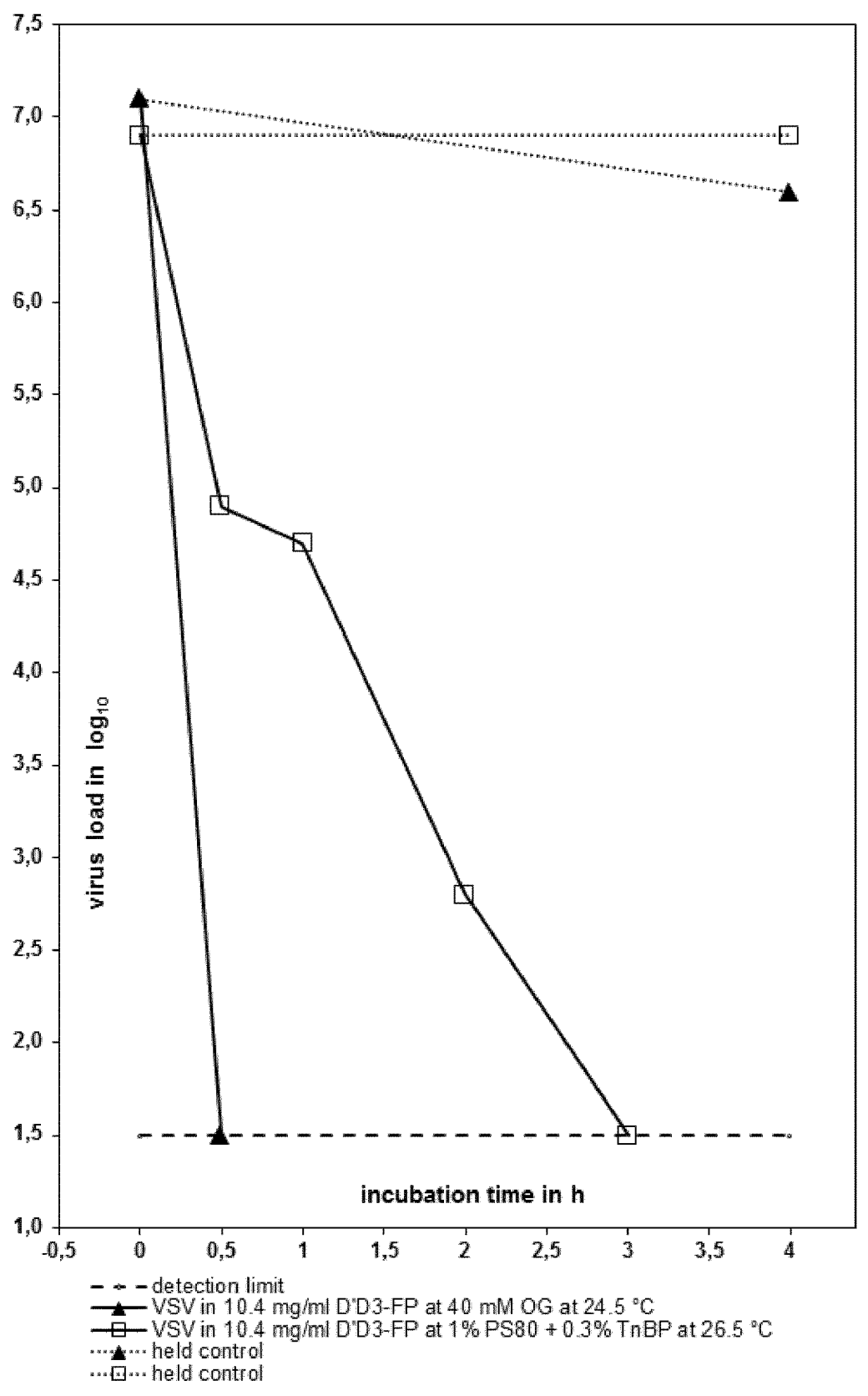
Figure 13:
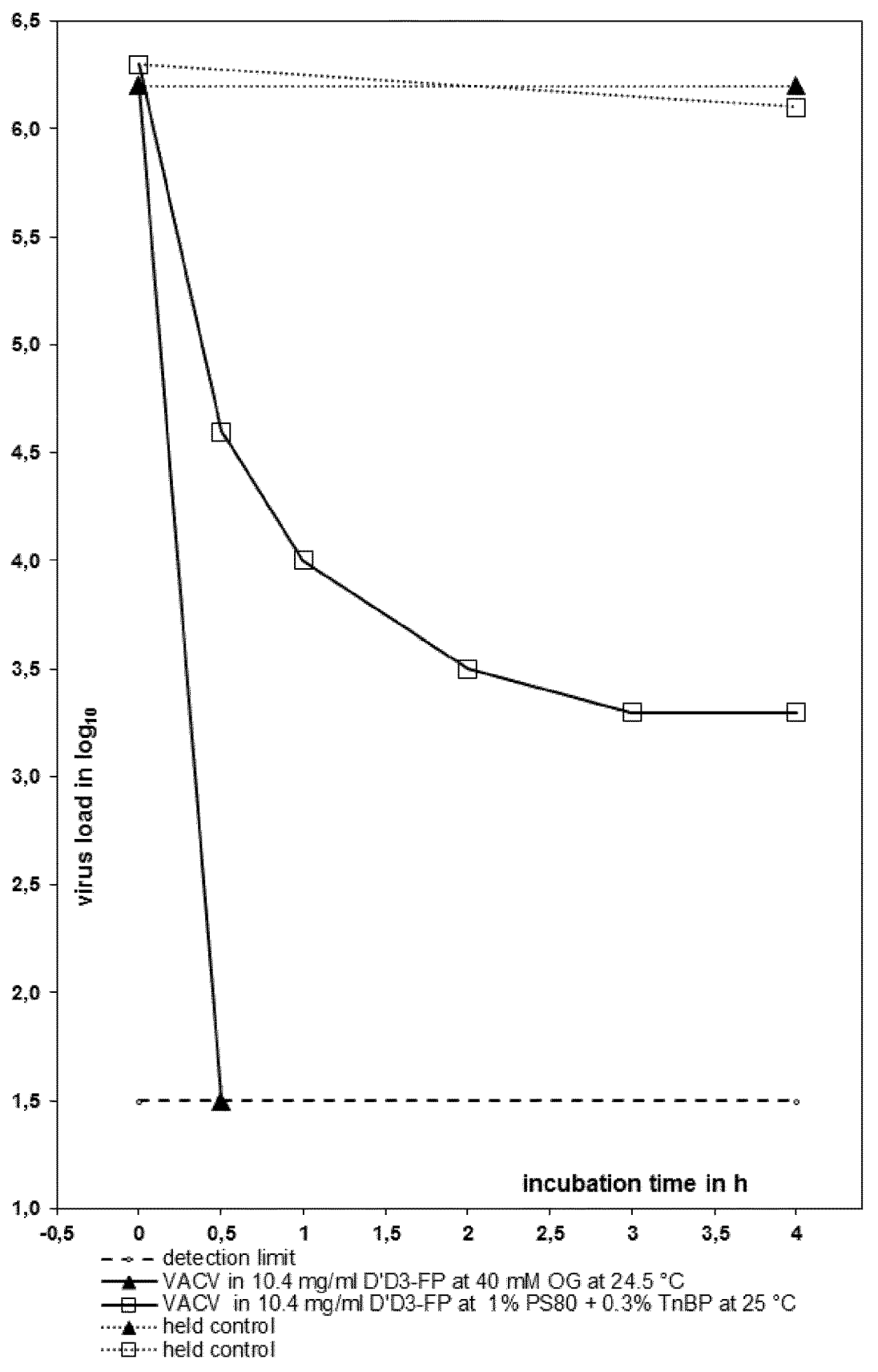

Furthermore, robustness studies with Vaccinia virus (VACV), the most resistant enveloped virus against SD inactivation [14] and Vesicular Stomatitis Virus (VSV) were studied. The results given in FIG. 12 (Table 10b) for VSV and in FIG. 13 (Table 10c) for VACV demonstrates a much faster virus inactivation by OG compared to SD (1% PS80+ 0.3% TnBP). Especially only OG completely inactivates VACV very fast where SD failed to inactivate VACV effectively over a period of 4 hours (FIG. 13).

TABLE 10b

VSV (Vesicular Stomatitis Virus) inactivation by SD compared to OG treatment

| time in minutes | VSV, 40 mM OG | held control | VSV, 1% PS80 + 0.3% Tn BP | held control |
|---|---|---|---|---|
| prior add | 7.1 | 7.1 | 6.9 | 6.9 |
| 30 | ≤1.5 | n.d. | 4.9 | n.d. |
| 60 | ≤1.5 | n.d. | 4.7 | n.d. |
| 120 | ≤1.5 | n.d. | 2.8 | n.d. |
| 180 | ≤1.5 | n.d. | ≤1.5 | n.d. |
| 240 | ≤1.5 | 6.6 | ≤1.5 | 6.9 |

TABLE 10c

VACV (Vaccinia) inactivation by SD compared to OG treatment

| time in minutes | VACV, 40 mM OG | held control | VACV, 1% PS80 + 0.3% Tn BP | held control |
|---|---|---|---|---|
| prior add | 6.2 | 6.2 | 6.3 | 6.3 |
| 30 | ≤1.5 | n.d. | 4.6 | n.d. |
| 60 | ≤1.5 | n.d. | 4.0 | n.d. |
| 120 | ≤1.5 | n.d. | 3.5 | n.d. |
| 180 | ≤1.5 | n.d. | 3.3 | n.d. |
| 240 | ≤1.5 | 6.2 | 3.3 | 6.1 |

CONCLUSION

The rapid inactivation kinetics observed indicate that OG and other alkyl-glycosides effectively and reliably inactivate enveloped viruses.

Immunoaffinity Chromatography (IAC) Experiments rD'D3-FP was treated with OG or PS80/TNBP before loading onto an IAC resin. For this purpose, the rD'D3-FP sample was diluted with OG stock solution (600 mM) to yield a virus inactivation solution including 60 mM OG. In a control experiment, PS80/TNBP stock solution (3% PS80/0.9% TNBP) was added to yield a final concentration of 1% PS80, 0.3% TNBP. Solutions were then filtered and incubated at room temperature for 2 hours. Subsequently, IAC experiments were carried out according to Table 11. For chromatography, the immunoaffinity resin CaptureSelect Human Albumin (ThermoFisher) was used. The chromatography unit used was an ÄKTA Avant system (GE Healthcare).

TABLE 11

Experimental conditions for immunoaffinity chromatography.

| Step | Description |
|---|---|
| 1 | equilibration of column with 20 mM Tris, 10 mM EDTA pH 7.4 |
| 2 | Loading of 11 mg virus inactivated rD'D3-FP/mL resin, conditioned with EDTA stock solution to a final concentration of 9 mM EDTA |
| 3 | post-load wash with 20 mM Tris, 10 mM EDTA pH 7.4 (10 column volumes (CV)) |
| 4 | wash step 2 with 400 mM NaCl, 20 mM sodium phosphate pH 6.3 (5 CV) |
| 5 | pre-elution with 375 mM MgCl$_2$, 100 mM MES pH 6.0 (3 CV) |
| 6 | elution with 1M MgCl$_2$, 100 mM MES pH 6.0 (5 CV). Collection of two CV. |
| 7 | Column cleaning |

The PS80/TNBP treatment resulted in a significant loss of 60% rD'D3-FP in the pre-elution (step 5) fraction and only 40% rD'D3-FP was found in the eluate fraction. In contrast, the OG treatment gave much higher yields, and 83% of rD'D3-FP was present in the eluate fraction. Host cell DNA clearance in the eluate fraction (180 pg/mL) was 1700-fold across the purification step with OG. In other examples when different feedstock rD'D3-FP lots with higher concentrations of host cell DNA were incubated with OG, the host cell DNA content in the eluate of the immunoaffinity chromatography step were comparable resulting in purification factors of about 25,000. Compared to PS80/TNBP treatment, OG treatment yielded 7.4-fold better host cell DNA clearance. Normalized host cell protein clearance across this step was 1270-fold for OG-treated sample, resulting in 117 ppm in the eluate (1.9-fold better compared to PS80/TNBP treatment). To allow better comparability between the eluate fractions at the same rD'D3-FP concentrations after detergent or solvent/detergent treatment, step 5 (Table 11) was omitted from the protocol in a second set of experiments to avoid splitting of the rD'D3-FP in the case of PS 80/TNBP-treated feed material into two fractions.

Immunoaffinity Chromatography (IAC) Experiments (without Pre-Elution Step 5)

rD'D3-FP was treated with 60 mM OG or other alkyl glycosides as specified in Table 12, 1% PS 80, 0.3% TNBP or a buffer control (500 mM NaCl, 20 mM Tris pH 7.4). Solutions were then filtered and incubated at room temperature for 2 hours.

TABLE 12

Overview alkyl glycosides used for incubation pre immunoaffinity purification.

| Alkyl glycoside | Stock concentration (in 500 mM NaCl, 20 mM Tris pH 7.4) | Final concentration after mixing |
|---|---|---|
| n-octyl-beta-D-glucopyranoside (OG) | 600 mM | 60 mM |
| n-decyl-beta-D-glucopyranoside (DG) | 600 mM | 60 mM |
| | 50 mM | 5 mM |
| n-dodecyl-beta-D-glucopyranoside (DDG) | 5 mM | 0.5 mM |
| n-octyl-beta-D-maltoside (OM) | 600 mM | 60 mM |
| n-decyl-beta-D-maltoside (DM) | 600 mM | 60 mM |
| | 50 mM | 5 mM |
| n-dodecyl-beta-D-maltoside (DDM) | 600 mM | 60 mM |
| | 5 mM | 0.5 mM |

After 2 hours incubation, the virus inactivated samples were loaded onto a chromatography column packed with CaptureSelect Human Albumin (ThermoFisher) resin. The chromatography unit used was an ÄKTA Avant system (GE Healthcare). The chromatography protocol is described in Table 11, step 5 was omitted in this set of experiments in order to avoid yield loss in the PS80/TNBP treated fractions.

Figure 10:
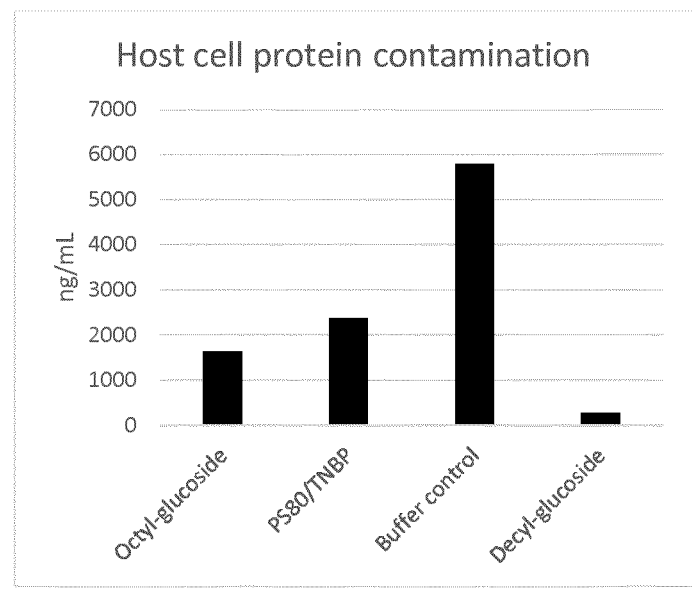
FIG. 10 compares: a) the residual host cell protein concentration in samples of an albumin fusion protein (rD'D3-FP) obtained by immunoaffinity chromatography following treatment with n-octyl-β-D-glucopyranoside (OG), n-decyl-β-D-glucopyranoside (DG), polysorbate 80 and tri-n-butylphosphate (PS80/TNBP) or buffer control; and b) the relative improvement of host cell protein clearance (fold improvement of HCP clearance) when OG or DG are used in step ii) compared to PS80/TNBP (clear bars) or buffer control (hatched bars) treatment.
Figure 10:
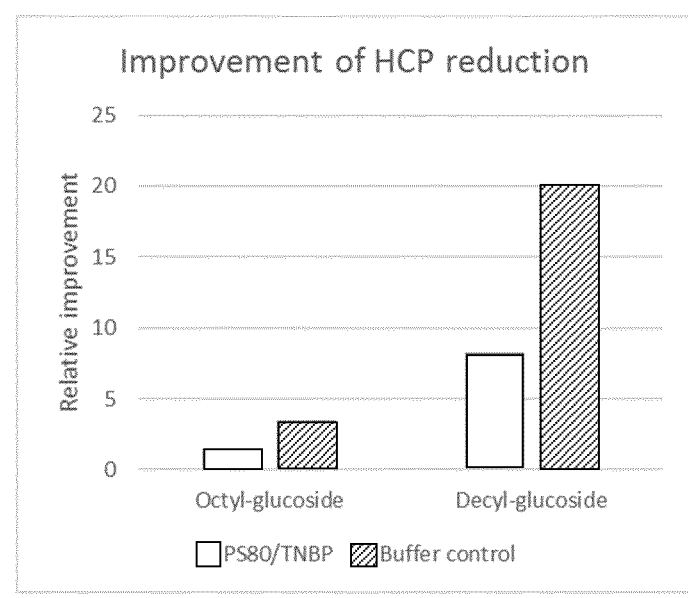
Figure 11:
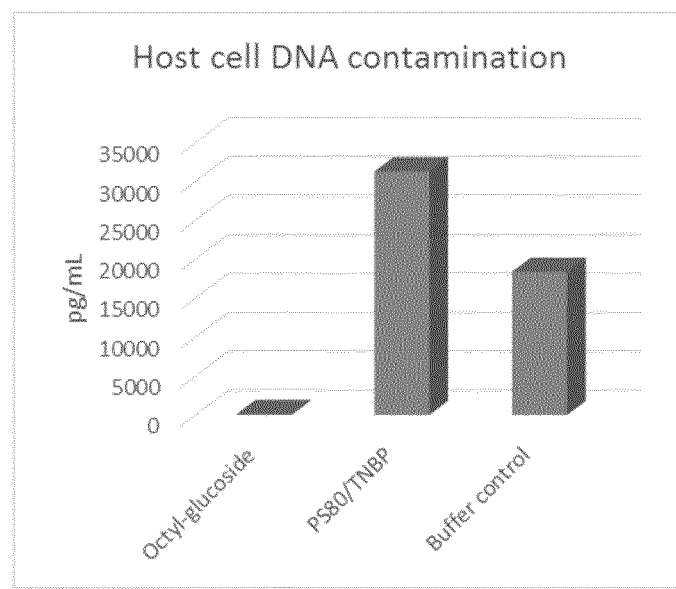
FIG. 11 compares: a) the residual host cell DNA concentration in samples of an albumin fusion protein (rD'D3-FP) obtained by immunoaffinity chromatography following treatment with n-octyl-β-D-glucopyranoside (OG), polysorbate 80 and tri-n-butylphosphate (PS80/TNBP) or buffer control; and b) the relative improvement of host cell DNA clearance (fold improvement of host cell DNA clearance) when OG is used compared to PS80/TNBP (clear bar) or buffer control (striped bar) treatment.
Figure 11:
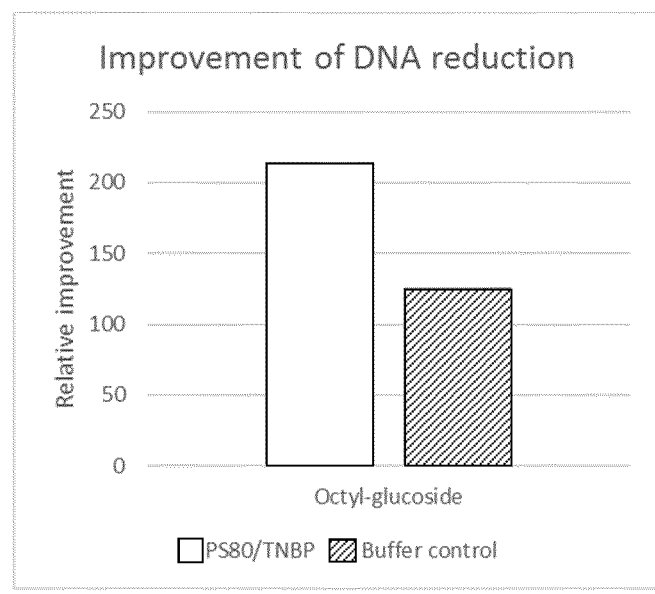

All treatment options resulted in comparable yields and protein concentrations of rD'D3-FP in the eluate fractions which were analysed for host cell DNA (HC DNA) and protein (HCP) (Table 13, FIGS. 10a and 11a).

TABLE 13

Overview analytical data obtained with different alky glycosides and control.

| Eluate fractions | HC DNA/pg/mL | HC DNA/ppm | HC DNA step reduction | HCP ng/mL | Normalized dHCP (ppm) | HCP step reduction |
|---|---|---|---|---|---|---|
| Buffer control | 18419 | 2091 | 16 | 5792 | 657 | 226 |
| OG 60 mM | 146 | 17 | 1978 | 1649 | 187 | 794 |
| OM 60 mM | 18672 | 2425 | 15 | 2914 | 379 | 392 |
| DG 60 mM | 50030 | 7829 | 6 | 288 | 45 | 3300 |
| DG 5 mM | 28401 | 3235 | 10 | 6528 | 744 | 200 |
| DM 60 mM | 28417 | 3593 | 10 | 4283 | 541 | 274 |
| DM 5 mM | 29649 | 4001 | 10 | 4478 | 535 | 278 |
| DDG 0.5 mM | 20149 | 2577 | 14 | 12119 | 1551 | 96 |
| DDM 60 mM | 37381 | 5065 | 8 | 5560 | 753 | 197 |
| DDM 0.5 mM | 24566 | 2863 | 12 | 9154 | 1068 | 139 |
| PS80/TNBP | 31293 | 3246 | 9 | 2381 | 247 | 601 |

Results for host cell DNA were comparable or slightly worse compared to buffer control for all samples except when 60 mM OG were used. This led to an eluate sample with particularly low host cell DNA content which was 126-fold lower than in buffer control and 214-fold lower than in the PS80/TNBP control (FIG. 11b). Host cell DNA was cleared by a factor of about 2000 in this particular example (DNA levels normalized to protein content).

Similarly, in comparison to the buffer control treatment, the OG treatment led to a 3.5-fold better reduction in levels of host cell protein. Normalized to rD'D3-FP content, the HCP reduction across the purification step was 725-fold. If PS80/TNBP was used the HCP clearance was 32% diminished compared to OG (Table 13, FIG. 10b). Of the other alkyl glycosides tested, only DG and OM at 60 mM improved HCP clearance compared to buffer control. For OM the effect was small (1.7-fold), whereas for DG a 14.6-fold improvement was found. This effect was strongly concentration dependent, as at 5 mM DG HCP content in the eluate was comparable to buffer control.

In summary, the incubation of rD'D3-FP with OG prior to the following chromatography step yields an eluate sample which is significantly purer compared to buffer or PS80/TNBP control with respect to host cell DNA and host cell protein. OG treatment also allowed to use an additional wash step (Table 1, step 5) which in case of PS80/TNBP treatment yielded significant losses.

Example 2

Viral Inactivation Capacity of a Variety of Alkyl Glycosides

SUMMARY

Further laboratory studies were conducted similar to those described in Example 1 to assess the virus inactivation capacity of alkyl glycosides in addition to OG. n-octyl-beta-D-glucopyranoside, n-decyl-beta-D-glucopyranoside, n-octyl-beta-D-maltoside, n-dodecyl-beta-D-maltoside, n-dodecyl-beta-D-glucopyranoside and n-decyl-beta-D-maltoside were all found to be effective (FIG. 8) as well as at lower concentrations (about twice as high as their CMC values, FIG. 9).

It will be understood that the invention has been described by way of example only and modifications may be made whilst remaining within the scope and spirit of the invention.

Example 3

Reducing Process-Related Impurities by Using a Wash Step Containing OG

SUMMARY

Additional studies were performed to evaluate using alkyl glycosides as wash agents in a chromatography setup and study the effect on process-related impurity, in particular protein impurity clearance. In this example cell-free harvest material of rD'D3-FP from a bioreactor process was loaded onto an anion exchange column (Poros XQ, Thermo Scientific). rD'D3-FP is expressed together with the von Willebrand factor (VWF) propeptide which is cleaved off in the cells but secreted along with rD'D3-FP into the cell supernatant and is, therefore, present at levels comparable to the product. Hence, reducing the levels of this protein impurity is important. The chromatography protocol was modified and OG added to one of the wash buffers.

Method and Results

The purification details of the anion exchange chromatography can be found in Table 14. Two experiments were carried out. In option 1, step 5 (wash step 2) was performed without OG, in option 2 60 mM OG was additionally included in the wash buffer.

TABLE 14

Experimental conditions for immunoaffinity chromatography.

| Step | Description |
|---|---|
| 1 | Equilibration of column with 20 mM Tris, 50 mM NaI pH 7.5 |
| 2 | Loading of approx. 20 mg rD'D3-FP/mL resin |
| 3 | Post-load wash with 20 mM Tris, 50 mM NaCl pH 7.5 (5 column volumes (CV)) |
| 4 | Wash step 1 with 50 mM MES, 10 mM sodium citrate, 50 mM NaCl, pH 6.0 (15 CV) |
| 5 | Wash step 2 with<br>Option 1: 20 mM Tris, 50 mM NaCl, 10 mM EDTA, pH 7.5 (15 CV)<br>Option 2: 20 mM Tris, 50 mM NaCl, 10 mM EDTA, 60 mM OG, pH 7.5 (15 CV) |
| 6 | Linear elution from 50 to 500 mM NaCl in 60 mM Tris, 10 mM EDTA, pH 7.5 (5 CV). Collection of three CV. |
| 7 | Column cleaning |

The addition of OG in the wash step reduced the content of the VWF propeptide, a major protein impurity, significantly (see Table 15).

TABLE 15

Analytical results for main elution fractions of experiments with and without OG in the wash buffer.

| Wash step 2 buffer | Amount VWF propeptide in harvest (relative to rD'D3-FP) | Amount VWF propeptide in eluate (relative to rD'D3-FP) | Reduction factor (relative to harvest material) |
| --- | --- | --- | --- |
| No OG | 892,985 ppm | 1,041,885 ppm | None |
| 60 mM OG | 919,508 ppm | 6,228 ppm | 148 |

Without the addition of OG, the VWF propeptide was not separated at all from rD'D3-FP. Upon addition of 60 mM OG to wash step 2, the concentration of VWF propeptide in the eluate was reduced almost 150-fold. As the OG presence in wash step 2 was the only variable in these experiments, the improved protein impurity clearance can be attributed to it.

REFERENCES

[1] WHO Technical Report, Annex 4 *Guidelines on viral inactivation and removal procedures intended to assure the viral safety of human blood plasma products* Series No. 924, p 151-224, (2004).
[2] Korneyeva et al. (2002) *Biologicals*. 30(2):153-62.
[3] Lebing et al. (2003) *Vox Sang*. 84(3):193-201.
[4] Johnston et al. (2003) *Biologicals*. 31(3):213-21.
[5] Bosley et al. (2008) *Proteomics Clin Appl*. 2(6):904-7.
[6] WO 2015/073633
[7] WO 2016/188907
[8] Microfiltration and Ultrafiltration: Principles and Applications, L. Zeman and A. Zydney (Marcel Dekker, Inc., New York, N.Y., 1996).
[9] Ultrafiltration Handbook, Munir Cheryan (Technomic Publishing, 1986; ISBN No. 87762-456-9).
[10] Millipore catalogue entitled "Pharmaceutical Process Filtration Catalogue" pp. 177-202 (Bedford, Mass., 1995/96).
[11] Remington's Pharmaceutical Sciences, 16th edition (Osol, ed. 1980).
[12] Almeida & Alpar (1996) *J. Drug Targeting* 3:455-467.
[13] Gröner et al. (2012) Transfusion 52: 2104-2112
[14] Roberts (2000) Biologicals 28: 29-32.

The invention claimed is:

1. A method for purifying a recombinant polypeptide comprising the steps of: i) providing a solution comprising the recombinant polypeptide; ii) adding an alkyl glycoside to the solution; and iii) purifying the recombinant polypeptide by carrying out a step of chromatography on the solution.

2. The method of claim 1, wherein the alkyl glycoside is additionally included in the wash buffer of the chromatography step.

3. The method of claim 1, wherein step (iii) results in separation of the recombinant polypeptide from host cell DNA and/or host cell protein in the solution and/or from other protein impurities in the solution.

4. The method of claim 3, wherein step (iii) results in improved separation of the recombinant polypeptide from host cell DNA and/or host cell protein in the solution compared to the same process without adding the alkyl glycoside to the solution.

5. The method of claim 1, wherein the chromatography is immunoaffinity chromatography, affinity chromatography, hydrophobic interaction chromatography, ion exchange chromatography, multimodal chromatography, size exclusion chromatography, or metal chelate chromatography.

6. The method of claim 5, wherein the chromatography is immunoaffinity chromatography.

7. The method of claim 1, wherein an ion exchange chromatography step is carried out on the solution before the step of adding the alkyl glycoside to the solution.

8. The method of claim 1, wherein a hydrophobic interaction chromatography step is carried out on the solution after step (iii), and/or wherein a multimodal chromatography step is carried out on the solution after step (iii).

9. The method of claim 8, wherein an ion exchange chromatography step is carried out on the solution after the hydrophobic interaction or multimodal chromatography step.

10. The method of claim 1, wherein the method is for separating the recombinant polypeptide from host cell DNA and/or host cell protein and comprises the steps of: a) providing the solution comprising the recombinant polypeptide; b) purifying the recombinant polypeptide by carrying out a step of ion exchange chromatography on the solution; c) adding an alkyl glycoside to the solution; d) purifying the recombinant polypeptide by carrying out a step of immunoaffinity chromatography on the solution; e) purifying the recombinant polypeptide by carrying out a step of hydrophobic interaction or multimodal chromatography on the solution; and f) purifying the recombinant polypeptide by carrying out a further step of ion exchange chromatography on the solution.

11. The method of claim 5, wherein the ion exchange chromatography is anion exchange chromatography.

12. The method of claim 1, wherein the method provides a solution comprising a level of host cell DNA contamination that is less than 5000 pg/ml; and/or wherein the method provides a solution of the recombinant polypeptide comprising a level of host cell DNA contamination that is reduced by a factor of at least 1.5, when compared to a reference method in which no alkyl glycoside is used or a conventional S/D treatment is used.

13. The method of claim 1, wherein the method provides a solution comprising a level of host cell protein contamination that is less than 5000 ng/ml; and/or wherein the method provides a solution of the recombinant polypeptide comprising a level of host cell protein (HCP) contamination that is reduced by a factor of at least 1.5, when compared to a reference method in which no alkyl glycoside is used or a conventional S/D treatment is used.

14. The method of claim 1, wherein step ii) further comprises incubating the solution.

15. A method for inactivating one or more viruses in a solution comprising a step of adding an alkyl glycoside to the solution and incubating the solution.

16. The method of claim 15, wherein the solution is i) a solution comprising a recombinant polypeptide, or ii) plasma-derived material.

17. The method of claim 15, wherein the incubation is carried out for between 20 minutes and 5 hours.

18. The method of claim 15, wherein the incubation is carried out at room temperature or between 4° C. and 10° C.

19. The method of claim 15, wherein the final concentration of the alkyl glycoside before the incubation is above the critical micelle concentration (CMC) of the alkyl glycoside.

20. The method of claim 15, wherein the incubation is carried out without agitation.

21. The method of claim 1, wherein the recombinant polypeptide is from a cell line recombinantly producing the polypeptide.

22. The method of claim 1, wherein the recombinant polypeptide is a blood coagulation protein, albumin, an immunoglobulin, or a fusion protein.

23. The method of claim 1, wherein the solution in step (i) has between 0.1 pg/ml and 50 pg/ml of host cell DNA and/or between 50 μg/ml and 1000 μg/ml of host cell protein.

24. The method of claim 1, wherein the alkyl glycoside is n-octyl-beta-D-glucopyranoside, or is selected from the group consisting of n-decyl-beta-D-glucopyranoside, n-octyl-beta-D-maltoside, n-dodecyl-beta-D-maltoside, n-dodecyl-beta-D-glucopyranoside, and n-decyl-beta-D-maltoside.

25. The method of claim 1, wherein the solution is further treated after step (iii) and any additional purification steps by a step of viral filtration.

26. The method of claim 1, wherein the solution is further treated after step (iii) and any additional purification steps by one or more steps of ultrafiltration and/or diafiltration.

27. The method of claim 1, wherein further comprising mixing the purified recombinant polypeptide is mixed with a pharmaceutically-acceptable carrier to make a pharmaceutical composition.

28. The method of claim 1, wherein the alkyl glycoside is added without any organic solvent and/or the alkyl glycoside is added without any prior mixing with an organic solvent.

29. A solution comprising a recombinant polypeptide and an alkyl glycoside, wherein the solution is obtained from step ii) of the method of claim 1.

30. A solution comprising a purified recombinant polypeptide, wherein the solution is obtained by the method of claim 1.

31. A method for purifying a recombinant polypeptide comprising the steps of: i) providing a solution comprising the recombinant polypeptide, and ii) purifying the recombinant polypeptide by carrying out a step of chromatography on the solution, wherein an alkyl glycoside is included in the wash buffer of the chromatography step.

32. The method of claim 31, wherein step ii) results in separation of the recombinant polypeptide from host cell DNA, host cell protein, and/or other protein impurities in the solution.

33. The method of claim 32, wherein step ii) results in improved separation of the recombinant polypeptide from host cell DNA, host cell protein, and/or other protein impurities in the solution, as compared to a reference method in which the alkyl glycoside is not included in the wash buffer.

* * * * *